(12) United States Patent
Chiriva-Internati et al.

(10) Patent No.: US 9,272,014 B2
(45) Date of Patent: Mar. 1, 2016

(54) GALECTIN-3C COMBINATION THERAPY FOR HUMAN CANCER

(75) Inventors: Maurizio Chiriva-Internati, Lubbock, TX (US); Everardo Cobos, Lubbock, TX (US); Constance John, San Francisco, CA (US)

(73) Assignees: Texas Tech University System, Lubbock, TX (US); MandalMed, Inc., San Francisco, CA (US)

( * ) Notice: Subject to any disclaimer, the term of this patent is extended or adjusted under 35 U.S.C. 154(b) by 0 days.

(21) Appl. No.: 14/008,262

(22) PCT Filed: Mar. 29, 2012

(86) PCT No.: PCT/US2012/031268
§ 371 (c)(1),
(2), (4) Date: Apr. 16, 2014

(87) PCT Pub. No.: WO2012/135528
PCT Pub. Date: Oct. 4, 2012

(65) Prior Publication Data
US 2014/0243275 A1    Aug. 28, 2014

Related U.S. Application Data

(60) Provisional application No. 61/468,798, filed on Mar. 29, 2011.

(51) Int. Cl.
| | |
|---|---|
| A61K 38/00 | (2006.01) |
| A61P 35/00 | (2006.01) |
| A61K 38/17 | (2006.01) |
| A61K 45/06 | (2006.01) |
| A61K 38/05 | (2006.01) |
| A61K 31/407 | (2006.01) |
| A61K 31/69 | (2006.01) |
| A61K 38/07 | (2006.01) |

(52) U.S. Cl.
CPC ........... *A61K 38/1732* (2013.01); *A61K 31/407* (2013.01); *A61K 31/69* (2013.01); *A61K 38/05* (2013.01); *A61K 38/07* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 5,780,454 A | 7/1998 | Adams | |
| 6,297,217 B1 | 10/2001 | Adams | |
| 6,617,317 B1 | 9/2003 | Adams | |
| 6,747,150 B2 | 6/2004 | Adams | |
| 6,770,622 B2 | 8/2004 | Jarvis | |
| 7,417,042 B2 | 8/2008 | Smyth | |
| 7,511,156 B2 | 3/2009 | Corey | |
| 7,691,896 B2 | 4/2010 | Myers | |
| 7,842,814 B2 | 11/2010 | Ling | |
| 7,981,917 B2 * | 7/2011 | Schonthal et al. | 514/406 |
| 2003/0054982 A1 * | 3/2003 | Jarvis et al. | 514/8 |
| 2009/0062227 A1 * | 3/2009 | Schonthal et al. | 514/44 |
| 2009/0110688 A1 | 4/2009 | Fertig et al. | |
| 2009/0182027 A1 | 7/2009 | Palladino et al. | |

OTHER PUBLICATIONS

Abdelrahim, et al. "Angiogenesis: an update and potential drug approaches" (review). Int J Oncol 2010; 36:5-18.
Acosta-Rodriguez EV, et al. "Galectin-3 mediates IL-4-induced survival and differentiation of B cells: functional cross-talk and implications during Trypanosoma cruzi infection" J Immunol 2004; 172:493-502.
Agrwal N, et al. "Carbohydrate-binding protein 35. I. Properties of the recombinant polypeptide and the individuality of the domains" J Biol Chem 1993; 268:14932-9.
Alsayed Y, et al. "Mechanisms of regulation ofCXCR4/SDF-1 (CXCL12)-dependent migration and homing in multiple myeloma" Blood 2007; 109:2708-17.
Anargyrou K, et al. "Novel anti-myeloma agents and angiogenesis" Leuk Lymphoma 2008; 49:677-89.
Balasubramanian K, et al. "Galectin-3 in urine of cancer patients: stage and tissue specificity" J Cancer Res Clin Oncol2009; 135:355-63.
Barondes SH, et al. "Galectins. Structure and function of a large family of animal lectins" J Biol Chem 1994; 269:20807-10.
Bergsagel DE, "Plasma cell myeloma: biology and treatment" Annu Rev Med 1991;42:167-78.
Bernardes ES, et al. "Toxoplasma gondii infection reveals a novel regulatory role for galectin-3 in the interface of innate and adaptive immunity" Am J Pathol 2006; 168:1910-20.
Blade J, et al.: "Allogenic bone marrow transplantation in multiple myeloma. Analysis of 12 consecutive cases". Med Clin (Barc) 1995; 105:1-4.
Bleul CC, et al. The lymphocyte chemoattractant SDF-1 is a ligand for LESTR/fusin and blocks HIV-1 entry Nature 1996; 382:829-33.
Bresalier RS, et al. "Colon cancer mucin: a new ligand for the beta•galactoside-binding protein galectin-3" Cancer Res 1996;56:4354-7.
Buttery R, et al. "Galectin-3: differential expression between small•cell and non-small-celllung cancer" Histopathology 2004; 44:339-44.
Byrd JC, et al. "Mucins and mucin binding proteins in colorectal cancer" Cancer Metastasis Rev 2004; 23:77-99.

(Continued)

*Primary Examiner* — Marcela M Cordero Garcia
(74) *Attorney, Agent, or Firm* — Edwin S. Flores; Chainey P. Singelton; Chalker Flores, LLP

(57) ABSTRACT

The present invention provides a novel composition of matter useful for the treatment of neoplastic diseases. The novel composition is synergistic and comprised of galectin-3C in combination with a proteosome inhibitor, the combination having a pharmacologic activity greater than the expected additive effect of its individual components. Other embodiments of the invention provide novel synergistic compositions of galectin-3C with a proteasome inhibitor capable of reducing or overcoming resistance that develops to the proteasome inhibitor or reducing the adverse side effects from the proteasome inhibitor through increasing the therapeutic efficacy of lower doses.

13 Claims, 11 Drawing Sheets

(56) References Cited

OTHER PUBLICATIONS

Chauhan D, et al. "The bortezomib/proteasome inhibitor PS-341 and triterpenoid CDDO-Im induce synergistic anti•multiple myeloma (MM) activity and overcome bortezomib resistance" Blood 2004;103:3158-66.

Chauhan D, et al. "Targeting mitochondria to overcome conventional and bortezomib/proteasome inhibitor PS-341 resistance in multiple myeloma (MM) cells" Blood 2004;104:2458-66.

Chauhan D, et al. "Combination of novel proteasome inhibitor NPI-0052 and lenalidomide trigger in vitro and in vivo synergistic cytotoxicity in multiple myeloma" Blood 2010;115:834-45.

Clark AG, et al. "Multifunctional regulators of cell growth are differentially expressed in anergic murine B cells" Mol Immunol 2007; 44:1274-85.

Cvejic D, et al. "Galectin-3 and carcinoembryonic antigen expression in medullary thyroid carcinoma: possible relation to tumour progression" Histopathology 2000;37:530-5.

Davies AM, et al. "Incorporating bortezomib into the treatment of lung cancer" Clin Cancer Res 2007; 13:s4647-51.

Davies AM, et al. "Phase I study of two different schedules of bortezomib and pemetrexed in advanced solid tumors with emphasis on non-small cell lung cancer" J Thorac Oncol 2007; 2:1112-6 [abstract].

Einsele H. "Bortezomib" Recent Results Cancer Res 2010;184:173-87 [abstract].

Engelhardt M, et al., "Consensus statement from European experts on the diagnosis, management, and treatment of multiple myeloma: from standard therapy to novel approaches" Leuk Lymphoma 2010.

Fernandez PL, et al. "Galectin-3 and laminin expression in neoplastic and non-neoplastic thyroid tissue" J Pathol1997; 181:80-6.

Hasan SS, et al. "Galectins- potential targets for cancer therapy" Cancer Lett 2007;253:25-330.

Hideshima T, et al. "Biologic sequelae of IKB kinase (IKK) inhibition in multiple myeloma: therapeutic implications" Blood 2009;113:5228-36.

Hoyer KK, et al. "An anti-apoptotic role for galectin-3 in diffuse large B-celllymphomas" Am J Pathol 2004; 164:893-902.

Hsu DK, et al. "Biochemical and biophysical characterization of human recombinant IgE-binding protein, an S-type animal lectin" J. Biol. Chern. 1992; 267:14167-74.

Iurisci I, et al. "Concentrations of galectin-3 in the sera of normal controls and cancer patients" Clin Cancer Res 2000; 6:1389-93.

John CM, et al. "Truncated galectin-3 inhibits tumor growth and metastasis in orthotopic nude mouse model of human breast cancer" Clin Cancer Res 2003; 9:2374-83.

Kawachi K, et al. "Galectin-3 expression in various thyroid neoplasms and its possible role in metastasis formation" Hum Pathol2000; 31:428-33.

Grothey, A et al. "Targeting angiogenesis: progress with anti-VEGF treatment with large molecules" Nat Rev Clin Oncol2009; 6:507-18.

Kotla V, et al. "Mechanism of action of lenalidomide in hematological malignancies" J Hematol Oncol 2009; 2:36.

Kuklinski, S, et al., "Homophilic binding properties of galectin-3: involvement of the carbohydrate recognition domain" J Neurochem 1998; 70:814-23.

Laubach, JP, et al., "Clinical challenges associated with bortezomib therapy in multiple myeloma and Waldenstroms Macroglobulinemia" Leuk Lymphoma 2009;50:694-702.

Li, WW, et al. "Antiangiogenesis in haematological malignancies" BR J Haematol 2008; 143:622-31.

Liu, FT, et al. "Expression and function of galectin-3, a beta-galactoside-binding lectin, in human monocytes and macrophages" Am J Pathol1995; 147:1016-28.

Liu, FT, et al. "Modulation of functional properties of galectin-3 by monoclonal antibodies binding to the non-lectin domains" Biochemistry 1996; 35:6073-9.

Liu, FT, et al. "Galectins as modulators of tumour progression" Nat Rev Cancer 2005; 5:29-41.

Markowska, AI, et al. "Galectin-3 is an important mediator of VEGF- and bFGF•mediated angiogenic response" J Exp Med 2010.

Medinger, M, et al. "Vascular endothelial growth factor-related pathways in hemato-lymphoid malignancies" J Oncol 2010; 2010:729725.

Mehul B, et al. "Cross-linking of galectin 3, a galactose-binding protein of mammalian cells, by tissue-type transglutaminase" FEBS Lett 1995; 360:160-4.

Mina-Osorio, P, et al. "A role for galectin-3 in CD13-mediated homotypic aggregation of monocytes" Biochem Biophys Res Commun 2007; 353:605-10.

Mirandola, L. et al. Galectin-3C Inhibits Tumor Growth and Increases the Anticancer Activity of Bortezomib in a Murine Mode I of Human Multiple Myeloma Plos one, Jul. 13, 2011, vol. 6. pp. 1-14.

Mitsiades, CS et al. Antitumor effects of the proteasome inhibitor bortezomib in medullary and anaplastic thyroid carcinoma cells in vitro. J Clin Endocrinol Metab 2006; 91:4013-21.

Miyazaki, J et al. "Increased expression of galectin-3 in primary gastric cancer and the metastatic lymph nodes" Oncol Rep 2002; 9:1307-12.

Moschetta, M et al. "Bortezomib and zoledronic acid on angiogenic and vasculogenic activities of bone marrow macrophages in patients with multiple myeloma" Eur J Cancer 2010; 46:420-9.

Moschetta, M et al. Angiogenesis inhibitors: implications for combination with conventional therapies. Curr Pharm Des 2010; 16:3921-31.

Nakahara, S et al. "On the role of galectin-3 in cancer apoptosis" Apoptosis 2005;10:267-75.

Nangia-Makker, P et al. "Galectin-3 in apoptosis, a novel therapeutic target" J Bioenerg Biomembr 2007; 39:79-84.

Nangia-Makker, P et al. "Galectin-3 cleavage: a novel surrogate marker for matrix metalloproteinase activity in growing breast cancers" Cancer Res 2007; 67:11760-8.

Nieminen, J et al. "Visualization of galectin-3 oligomerization on the surface of neutrophils and endothelial cells using fluorescence resonance energy transfer" J Biol Chem 2007; 282:1374-83.

Ochieng, J et al. "Galectin-3 is a novel substrate for human matrix metalloproteinases-2 and -9" Biochemistry 1994; 33:14109-14.

Ochieng, J et al. "Modulation of the biological functions of galectin-3 by matrix metalloproteinases" Biochim Biophys Acta 1998; 1379:97-106.

Oda, Y et al. "Purification and characterization of beta-galactoside-binding lectin from chick embryonic skin" Biochim Biophys Acta 1983; 761:237-45.

Oishi, T et al. "Galectin-3 may contribute to Cisplatin resistance in clear cell carcinoma of the ovary" Int J Gynecol Cancer 2007; 17:1040-6.

Oliveira, FL et al. "Kinetics of mobilization and differentiation of lymphohematopoietic cells during experimental murine schistosomiasis in galectin-3 -/-mice" J Leukoc Biol 2007; 82:300-10.

Rajkumar, SV et al. "A review of angiogenesis and antiangiogenic therapy with thalidomide in multiple myeloma" Cancer Treat Rev 2000; 26:351-62.

Rajkumar, SV et al. "Thalidomide as initial therapy for early-stage myeloma" Leukemia 2003; 17:775-9.

Rana, C et al. "Bone marrow angiogenesis in multiple myeloma and its correlation with clinicopathological factors" Ann Hematol2010; 89:789-94.

Raz, A et al. "Lectin-like activities associated with human and murine neoplastic cells" Cancer Res 1981; 41:3642-7.

Richardson, PG et al. "Beyond single-agent bortezomib:combination regimens in relapsed multiple myeloma" Curr Opin Oncol2006;18:598-608. (Abstract).

Shah, MA et al. "A Multicenter, Phase II study of Bortezomib (PS-341) in patients with unreasonable or metastatic gastric and gastroesophageal junction adenocarcinoma" Invest New Drugs 2010.

Shin WS et al. "Soluble PTK7 inhibits tube formation, migration, and invasion of endothelial cells and angiogenesis" Biochem Biophys Res Commun 2008; 371:793-8.

Stenner, F et al. "Targeted therapeutic approach for an anaplastic thyroid cancer in vitro and in vivo" Cancer Sci 2008; 99:1847-52.

Sterz J, et al. "The potential of proteasome inhibitors in cancer therapy" Expert Opin Investig Drugs 2008;17:879-95.

(56) References Cited

OTHER PUBLICATIONS

Sugahara, T et al. "White sorghum (Sorghum bicolor (L.) Moench) bran extracts suppressed IgE production by U266 cells" Biosci Biotechnol Biochem 2009; 73:2043-7.

Swelam, WM et al. "Biological impact of vascular endothelial growth factor on vessel density and survival in multiple myeloma and plasmacytoma" Pathol Res Pract 2010; 206:753-9.

Takenaka, Y et al. "Malignant transformation of thyroid follicular cells by galectin-3" Cancer Lett 2003; 195:111-9.

Search Report and Written Opinion PCT/US2012/031268 {KIPO} dated Oct. 25, 2012.

Thijssen, VL et al. "Galectins in the tumor endothelium: opportunities for combined cancer therapy" Blood 2007; 110:2819-27.

Tsukamoto, S et al. "Targeting the proteasome pathway" Expert Opin Ther Targets 2009;13:605-21.

van den Brule, FA et al. "Transglutaminase-mediated oligomerization of galectin-3 modulates human melanoma cell interactions with laminin" Cell Adhes Commun 1998; 5:425-35.

Voortman, J et al. "The proteasomal and apoptotic phenotype determine bortezomib sensitivity of non-small cell lung cancer cells" Mol Cancer 2007;6:73.

Voortman, J et al. "A parallel dose-escalation study of weekly and twice-weekly bortezomib in combination with gemcitabine and cisplatin in the first-line treatment of patients with advanced solid tumors" Clin Cancer Res 2007; 13:3642-51.

Voutsadakis, IA, et al. "Additive inhibition of colorectal cancer cell lines by aspirin and bortezomib" Int J Colorectal Dis 2010;25:795-804.

Woo, HJ et al. "Carbohydrate-binding protein 35 (Mac-2), alaminin-binding lectin, forms functional dimers using cysteine 186" J Biol Chem 1991; 266:18419-22.

Zhao, Q et al. "Interaction between circulating galectin-3 and cancer-associated MUC1 enhances tumour cell homotypic aggregation and prevents anoikis" Mol Cancer 2010; 9:154.

Bataille, R et al. "Multiple myeloma" N Engl J Med 1997; 336:1657-64.

Dees, EC et al. "A phase I and pharmacologic study of the combination of bortezomib and pegylated liposomal doxorubicin in patients with refractory solid tumors" Cancer Chemother Pharmacol2008; 63:99-107.

Giatromanolaki, A et al. "Hypoxia and activated VEGF/receptor pathway in multiple myeloma" Anticancer Res 2010; 30:2831-6.

Kaur, Gumneet et al. "JS-K has potent anti-angiogenic activity in vitro and inhibits tumour angiogenesis in a multiple myeloma model in vivo" J Pharm Pharmacol 2010; 62:145-51.

Huang ZL et al. "Expression of galectin-3 in liver metastasis of colon cancer and the inhibitory effect of modified citrus pectin" Nan Fang Yi Ke Da Xue Xue Bao 2008;28:1358-61 [abstract].

\* cited by examiner

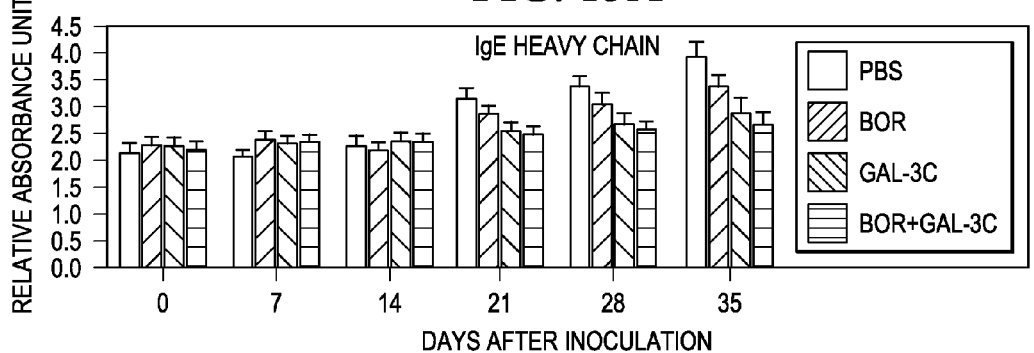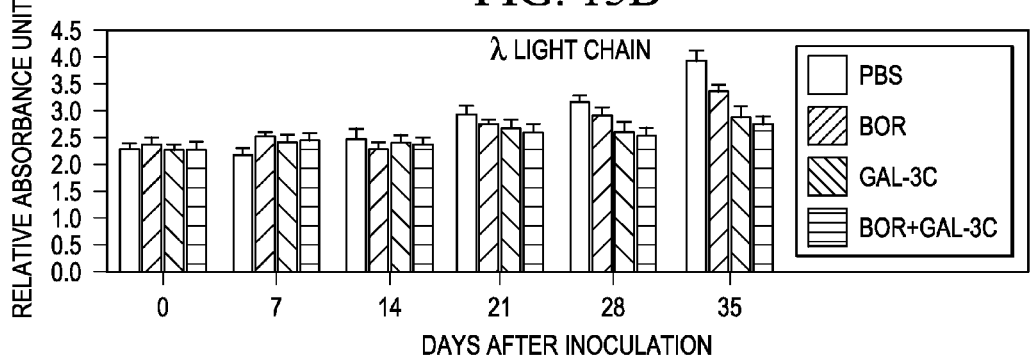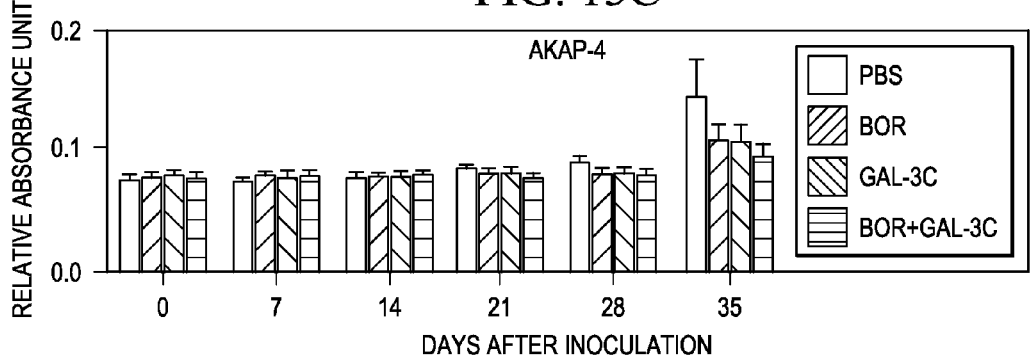

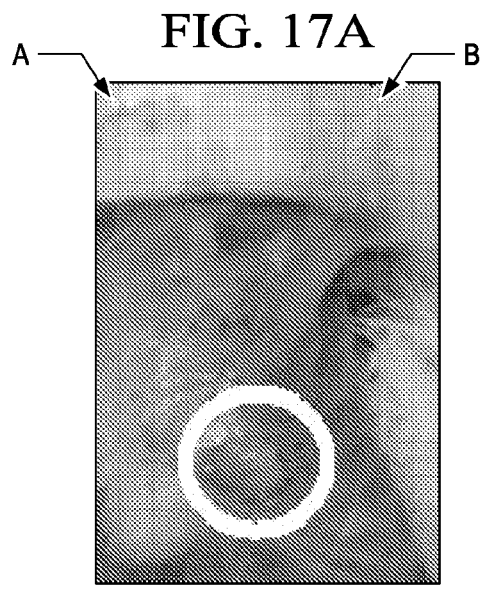
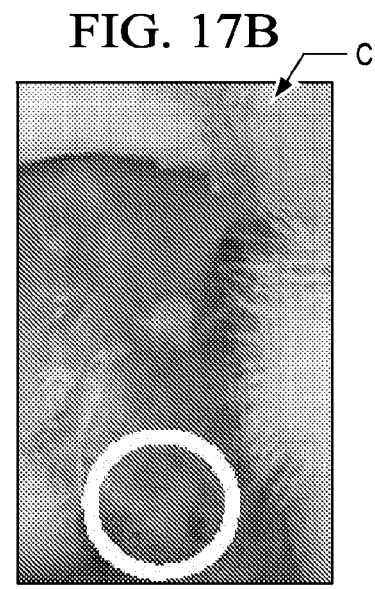
FIG. 17A  FIG. 17B
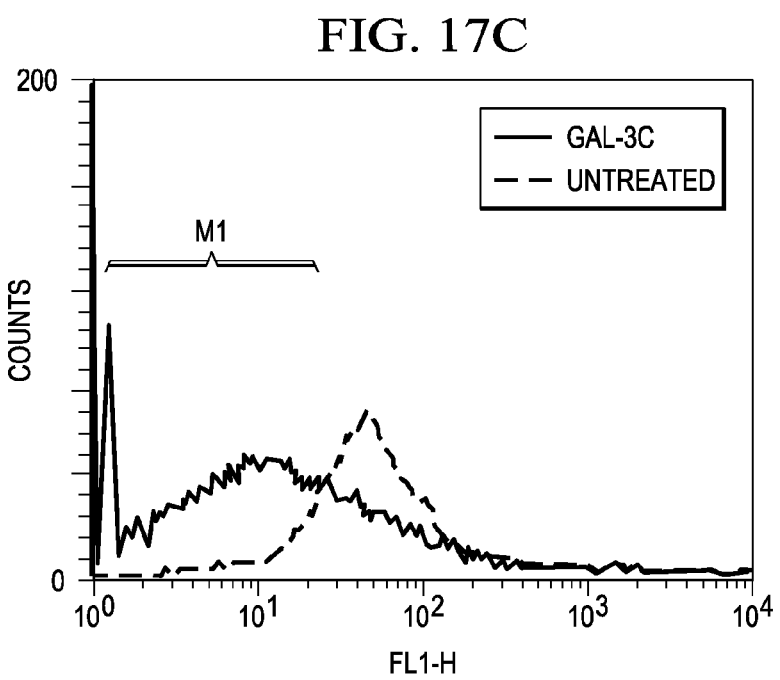
FIG. 17C

SEQUENCE LISTING

<160> NUMBER OF SEQ ID NOS: 6

<210> SEQ ID NO 1
<211> LENGTH: 143
<212> TYPE: PRT
<213> ORGANISM: artificial sequence
<220> FEATURE:
<223> OTHER INFORMATION: synthetic peptide

<400> SEQUENCE: 1

Gly Ala Pro Ala Gly Pro Leu Ile Val Pro Tyr Asn Leu Pro Leu Pro
1               5                   10                  15

Gly Gly Val Val Pro Arg Met Leu Ile Thr Ile Leu Gly Thr Val Lys
            20                  25                  30

Pro Asn Ala Asn Arg Ile Ala Leu Asp Phe Gln Arg Gly Asn Asp Val
        35                  40                  45

Ala Phe His Phe Asn Pro Arg Phe Asn Glu Asn Asn Arg Arg Val Ile
    50                  55                  60

Val Cys Asn Thr Lys Leu Asp Asn Asn Trp Gly Arg Glu Glu Arg Gln
65                  70                  75                  80

Ser Val Phe Pro Phe Glu Ser Gly Lys Pro Phe Lys Ile Gln Val Leu
                85                  90                  95

Val Glu Pro Asp His Phe Lys Val Ala Val Asn Asp Ala His Leu Leu
            100                 105                 110

Gln Tyr Asn His Arg Val Lys Lys Leu Asn Glu Ile Ser Lys Leu Gly
        115                 120                 125

Ile Ser Gly Asp Ile Asp Ile Thr Ser Ala Ser Tyr Thr Met Ile
    130                 135                 140

<210> SEQ ID NO 2
<211> LENGTH: 240
<212> TYPE: PRT
<213> ORGANISM: artificial sequence
<220> FEATURE:
<223> OTHER INFORMATION: synthetic peptide

<400> SEQUENCE: 2

Met Ala Asp Asn Phe Ser Leu His Asp Ala Leu Ser Gly Ser Gly Asn
1               5                   10                  15

Pro Asn Pro Gln Gly Trp Pro Gly Ala Trp Gly Asn Gln Pro Ala Gly
            20                  25                  30

Ala Gly Gly Tyr Pro Gly Ala Ser Tyr Pro Gly Ala Tyr Pro Gly Gln
        35                  40                  45

Ala Pro Pro Gly Ala Tyr Pro Gly Gln Ala Pro Pro Gly Ala Tyr His
    50                  55                  60

Gly Ala Pro Gly Ala Tyr Pro Gly Ala Pro Gly Val Tyr Pro
65                  70                  75                  80

Gly Pro Pro Ser Gly Pro Gly Ala Tyr Pro Ser Ser Gly Gln Pro Ser
                85                  90                  95

Ala Pro Gly Ala Tyr Pro Ala Thr Gly Pro Tyr Gly Ala Pro Ala Gly
            100                 105                 110

Pro Leu Ile Val Pro Tyr Asn Leu Pro Leu Pro Gly Gly Val Val Pro
        115                 120                 125

-continued

```
Arg Met Leu Ile Thr Ile Leu Gly Thr Val Lys Pro Asn Ala Asn Arg
    130                 135                 140

Ile Ala Leu Asp Phe Gln Arg Gly Asn Asp Val Ala Phe His Phe Asn
145                 150                 155                 160

Pro Arg Phe Asn Glu Asn Asn Arg Arg Val Ile Val Cys Asn Thr Lys
                165                 170                 175

Leu Asp Asn Asn Trp Gly Arg Glu Glu Arg Gln Ser Val Phe Pro Phe
                180                 185                 190

Glu Ser Gly Lys Pro Phe Lys Ile Gln Val Leu Val Glu Pro Asp His
            195                 200                 205

Phe Lys Val Ala Val Asn Asp Ala His Leu Leu Gln Tyr Asn His Arg
    210                 215                 220

Val Lys Lys Leu Asn Glu Ile Ser Lys Leu Gly Ile Ser Gly Asp Ile
225                 230                 235                 240

<210> SEQ ID NO 3
<211> LENGTH: 24
<212> TYPE: DNA
<213> ORGANISM: artificial sequence
<220> FEATURE:
<223> OTHER INFORMATION: synthetic oligonucleotide

<400> SEQUENCE: 3
gcgtactctg atactacaat gatg                                         24

<210> SEQ ID NO 4
<211> LENGTH: 19
<212> TYPE: DNA
<213> ORGANISM: artificial sequence
<220> FEATURE:
<223> OTHER INFORMATION: synthetic oligonucleotide

<400> SEQUENCE: 4
ggggttttgg gtaaagtca                                               19

<210> SEQ ID NO 5
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 5
cggtcgccac catggtgagc                                              20

<210> SEQ ID NO 6
<211> LENGTH: 21
<212> TYPE: DNA
<213> ORGANISM: artificial sequence
<220> FEATURE:
<223> OTHER INFORMATION: synthetic oligonucleotide

<400> SEQUENCE: 6
gagccgtacc tgctcgacat g                                            21
```

GALECTIN-3C COMBINATION THERAPY FOR HUMAN CANCER

FIELD OF INVENTION

The present invention relates in general to the field of clinical oncology and the drug therapy of human cancers, specifically to compositions of matter and methods of making and using compositions for treating cancers using a combination of galectin-3C and proteasome inhibitors.

BACKGROUND ART

The American Cancer Society expects more than 20,000 new cases of MM in the US in 2010. The median age at diagnosis is 69 years for men and 72 years for women (it rarely occurs before 40 years) and the median survival is 5 years (2). Multiple myeloma (MM) is a malignancy characterized by clonal proliferation and accumulation of terminally differentiated plasma B cells that produce immunoglobulin. The malignant plasma cells are found in the bone marrow (BM) and extramedullary locations (1). Currently chemotherapy induces complete tumor regression in about 50% of patients (1, 3), but the eventual outcome is the development of drug resistance and death. Thus, the need for more efficacious treatments is apparent.

The introduction of novel drugs such as thalidomide, lenalidomide, and bortezomib (Bor) that are thought to target specific intracellular pathways and affect cellular interactions with the tumor microenvironment, has aided in the treatment of MM especially in management of elderly patients (1,3). Nonetheless, although the recent advances in hematological diseases and especially in MM have prolonged survival and led to higher rates of remission, arguably the course of the disease has not fundamentally changed since the 1960s, when autologous hematopoietic stem cell transplantation (AHSCT) was first recommended as a standard treatment in patients that were suitable candidates for the procedure. The frontline treatment for MM is AHSCT, but the outcome is favorable only in younger patients where it increases the rate of complete remission and prolongs event-free survival compared with conventional chemotherapy (4). Thus, pharmacologic interventions are the only option for the majority of patients who are older.

During the last ten years, intriguing insights into the molecular mechanisms underlying the progression of MM were obtained and successfully translated into more effective therapeutics, such as the proteasome inhibitors. The ubiquitin-proteasome pathway degrades intracellular proteins, interacts with the cell cycle and apoptosis, and has an important function in almost all cellular events (5,6). The U.S. Food and Drug Administration (FDA) granted approval for the proteasome inhibitor bortezomib (PS-341; VELCADE®) for the treatment of multiple myeloma in May 2003. This was the first approval of a drug targeting the ubiquitin-proteasome pathway. Since then the FDA also has approved bortezomib for treatment of mantle cell lymphoma. Several U.S. Pat. Nos. 5,780,454; 6,297,217; 6,617,317; and 6,747,150, disclose (and each of which are incorporated herein by reference) the use of bortezomib for treatment of cancer (7-10).

The development of drug resistance frequently causes bortezomib to become ineffective in treatment of multiple myeloma and the drug also displays problematic off-target adverse effects (11,12). Combinations of bortezomib with other therapeutics are being tested to develop regimens that will overcome drug resistance and reduce the occurrence of adverse side effects (13-15).

Bortezomib (Bor) is a synthetic peptide boronate that is a reversible proteasome inhibitor. Several other classes of compounds that inhibit the proteasome have been developed that include several irreversible inhibitors (5,6). Salinosporamide A (NPI-0052) is a natural product that is an irreversible proteasome inhibitor that has been the subject of several U.S. Pat. Nos. 7,842,814; 7,511,156; and 7,691,896 (16-18). Synergy in animal models of multiple myeloma was shown for the combination of salinosporamide A and lenalidomide (19). Carfilzomib (PR-171) is an irreversible proteasome inhibitor. Carfilzomib is a synthetic epoxomycin analog that was previously disclosed in U.S. Pat. No. 7,417,042 by Smyth and Laidig (20). Three of the irreversible proteasome inhibitors, salinosporamide A, carfilzomib, and CEP-18770 (a bortezomib analog), are being tested in clinical trials.

Bor also has shown promising activity in some types of solid tumors, such as combination studies in non-small cell lung cancer (21-25). Other studies including clinical trials of Bor have indicated potential benefit in breast (25), gastrointestinal cancer (26,27), and thyroid cancer (28,29).

Galectin-3C (Gal-3C) is an N-terminally truncated form of the human carbohydrate binding protein, galectin-3. Galectin-3 is involved in cancer cell adhesive properties, metastatic and invasive potentials (30-33), tumor growth, neoplastic transformation, and apoptosis (34-36). Galectin-3 is a member of the galectin family that is defined based on sequence homology within the carbohydrate recognition domain (CRD) and a characteristic affinity for -galactosides (37,38). Galectin-3 is unique among the galectins because in addition to the carboxy-terminal CRD it has an amino-terminal domain that is critical for multivalent behavior. Alone the carboxy-terminal CRD lacks hemagglutination activity and the cooperative binding that are characteristics of the intact lectin. The amino-terminal domain enables the CRD to cross-link carbohydrate-containing ligands on cell surfaces and in the extracellular matrix and, thus, to modulate cell adhesion and signaling (39-43).

Galectin-3 is thought to participate in regulation of the inflammatory state of various immune cells. Several studies indicate that it plays a novel regulatory role in the B cell compartment (44-46) including PCs (47). Hoyer et al. found stage-specific expression during B-cell development (48). Highest galectin-3 levels were observed in the long-lived naive and memory B cells, and lowest were in germinal center and plasma B cells. Nonetheless, high level galectin-3 levels were observed in the neoplasms that derive from these cells-diffuse large B-cellymphoma, primary effusion lymphoma, and MM (48).

The expression of galectin-3 in cancer has been the subject of many studies. Among those cancers in which galectin-3 is overexpressed are non-small cell lung cancer (49), gastrointestinal cancer (50, 51, 52, Miyazaki, 2002 #2994, 53, 54), thyroid cancer (55-57), and ovarian cancer (58). The gene expression level of galectin-3 in three CCC cell lines was over threefold higher than that of ovarian serous adenocarcinoma cell lines. Knock-down of galectin-3 expression in clear cell carcinoma (CCC) of the ovary using small interfering RNA induced increased apoptosis induced by cisplatin, suggesting that galectin-3 expression may contribute to cisplatin-resistance in ovarian CCC (59).

The truncated galectin-3 (Gal-3C) disclosed in the present invention consists of 143 carboxy-terminal amino acid residues of human galectin-3. Gal-3C retains carbohydrate binding ability but lacks the amino-terminal domain and, therefore, is expected to act as a dominant negative inhibitor of galectin-3 by preventing its homophilic cross-linking that promotes cell adhesion and consequent survival signals (60).

The amino acid sequence of the galectin-3C, that is produced by exhaustive digestion with collagenase, and that is designated as SEQ ID NO: 1, is as follows: gap agplivpynl plpggvvprm litilgtvkp nanrialdfq rgndvafhfn prfnennrrv ivcntkldnn wgreerqsvf pfesgkpfki qvlvepdhfk vavndahllq ynhrvkklne isklgisgdi ditsasytmi (SEQ ID NO: 1)

The amino acid sequence of the intact recombinant human galectin-3 described by Oda et al. (61) is designated herein as SEQ ID NO: 2, and its sequence is as follows: madnfslhda lsgsgnpnpq gwpgawgnqp agaggypgas ypgaypgqap pgaypgqapp gayhgapgay pgapapgvyp gppsgpgayp ssgqpsapga ypatgpygap agplivpynl plpggvvprm litilgtvkp nanrialdfq rgndvafhfn prfnennrrv ivcntkldnn wgreerqsvf pfesgkpfki qvlvepdhfk vavndahllq ynhrvkklne isklgisgdi dltsasytmi (SEQ ID NO: 2)

Previously Gal-3C inhibited tumor growth and metastasis in a mouse model of human breast cancer and showed no evidence of adverse side effects (60). U.S. Pat. No. 6,770,622 to Jarvis et al. discloses the use of galectin-3C as set forth in SEQ ID No. 1 to treat cancer, to reduce tumor size, and to reduce metastasis (62).

SUMMARY OF THE INVENTION

The present invention provides a novel composition of matter comprised of galectin-3C and proteasome inhibitors such as bertozomib which are therapeutically useful in treatment of neoplastic disease. The total effect of the novel composition is greater than the sum of the effect of galectin-3C alone and the proteasome inhibitor alone. Thus, the present invention provides a novel method of treating neoplastic disease using the novel synergistic combinations of the present invention.

In one embodiment the present invention provides a pharmaceutical composition having therapeutic synergy effect comprising a galectin-3C in combination with an effective amount of a proteasome inhibitor selected from bortezomib, alinosporamide A or carfilzomib or a combination thereof. The galectin-3C and the proteasome inhibitor are administered separately or simultaneously. The galectin-3C and the proteasome inhibitor are administered immediately or by extended release. In one embodiment the present invention provides the proteasome inhibitor is the bortezomib. In one embodiment the present invention provides the proteasome inhibitor is the salinosporamide A. In one embodiment the present invention provides the proteasome inhibitor is the carfilzomib.

In one embodiment the present invention provides a pharmaceutical composition having therapeutic synergy comprising a galectin-3C in combination with an effective amount of a bortezomib, wherein the galectin-3C and bortezomib are administered separately or simultaneously. In one embodiment the composition is useful in treating cancer in vivo. The cancer is selected from the group consisting of non-small cell lung cancer, gastrointestinal cancer, breast cancer, thyroid cancer, and ovarian cancer.

In one embodiment the present invention provides a pharmaceutical composition having therapeutic synergy comprising galectin-3C in combination with an effective amount of a salinosporamide A or a carfilzomib, wherein the galectin-3C and the salinosporamide A or the carfilzomib, are administered separately or simultaneously. In one embodiment the galectin-3C and the salinosporamide A or carfilzomib are administered immediately or by extended release. In one embodiment the composition is useful in treating cancer in vivo, wherein said cancer is selected from the group consisting of non-small cell lung cancer, gastrointestinal cancer, breast cancer, thyroid cancer, and ovarian cancer.

In one embodiment the present invention provides a pharmaceutical composition comprising galectin-3C in combination with an effective amount of the proteasome inhibitor selected from a bortezomib, a salinosporamide A, or a carfilzomib wherein said galectin-3C and said proteasome inhibitor synergistically inhibit angiogenesis. In one embodiment the proteasome inhibitor is the bortezomib. In one embodiment the proteasome inhibitor is the salinosporamide A. In one embodiment the proteasome inhibitor is the carfilzomib. In one embodiment the proteasome inhibitor is 2 selected from the bortezomib, the salinosporamide A, or the carfilzomib. In one embodiment the proteasome inhibitor is the bortezomib, the salinosporamide A, and the carfilzomib.

In one embodiment the present invention provides a pharmaceutical composition comprising galectin-3C in combination with an effective amount of the proteasome inhibitor, salinosporamide A, or carfilzomib, wherein said galectin-3C and said proteasome inhibitor, salinosporamide A, or carfilzomib, synergistically inhibit angiogenesis.

In one embodiment the present invention provides the use of a galectin-3C in combination with an effective amount of the proteasome inhibitor, bortezomib, wherein the galectin-3C and bortezomib are administered separately or simultaneously for the preparation of a medicament for treating a mammal suffering from or susceptible to multiple myeloma.

In one embodiment the present invention provides the use of a galectin-3C in combination with an effective amount of the proteasome inhibitor, bortezomib, wherein the galectin-3C and bortezomib are administered separately or simultaneously for the preparation of a medicament for treating a mammal suffering from or susceptible to mantle cell lymphoma.

In one embodiment the present invention provides the use of a galectin-3C in combination with an effective amount of the proteasome inhibitor, salinosporamide A, or carfilzomib, wherein the galectin-3C and salinosporamide A, or carfilzomib, are administered separately or simultaneously for the preparation of a medicament for treating a mammal suffering from or susceptible to multiple myeloma.

In one embodiment the present invention provides the use of a galectin-3C in combination with an effective amount of the proteasome inhibitor, salinosporamide A, or carfilzomib, wherein the galectin-3C and salinosporamide A, or carfilzomib are administered separately or simultaneously for the preparation of a medicament for treating a mammal suffering from or susceptible to mantle cell lymphoma.

BRIEF DESCRIPTION OF THE DRAWINGS

FIGS. 7A and 7B are graphs of the results from proliferation assays with ARP-1, ARK-B, U266, and 8226/Dox, MM-1S, MM-RL, NCI-H929, and RMPI-8266 cells with 0.5, 1, 2, or 4 f-lg/ml Gal-3C compared to control wells over 48 h.

FIG. 9A is a map of the AAV/GFP expression vector showing the restriction sites Xba I and Not I used to insert the GFP coding sequence. FIG. 9B is an image of the ligation of AAV genome and GFP is shown. The GFP insert was cut out from AAV/GFP by Xba I and Not I restriction enzymes (lane 2). FIG. 9C is a graph of the quantification of virus titers by real-time PCR FIG. 9D is a plot of the identification of U266 cells transduced with AAV/GFP by flow cytometry. Grey and black histograms indicate the fluorescence intensity distribution of AAV/GFP- and AAV-transduced U266 cells, respectively. FIG. 9E is a plot of RT-PCR for GFP expression in transduced U266 cells. M: Marker, 1: AAV/GFP plasmid, 2: No RT 3: No template, 4: U266 cells transfected with AAV/GFP. The size of the band from lane 4 was the same as the lane 1. FIG. 9F is an image of the photomicrograph of U266 cells showing fluorescence of AAV/GFP-transduced U266 cells.

(FIG. 13$ii$) untreated vehicle-only control. (FIG. 13$iii$) Bor, (FIG. 13$iv$) Gal-3C treated; and (FIG. 13$v$) Gal-3C plus Bor.

FIGS. 15A-15C are graphs of ELISA for human immunoglobulins and AKAP-4 in mice sera The mice were bled at the indicated time point after inoculation of U266 cells, and the levels of igE heavy (FIG. 15A) and light chains (FIG. 15B), and AKAP-4 (FIG. 15C), were determined by ELISA. Each graph is representative of three studies with samples analyzed in triplicates.

FIGS. 17A-17C are images of representative untreated (FIG. 17A) and Gal-3C treated (FIG. 17B) tumor-bearing nude mice. Arrows indicate s.c. vascularization near tumors shown by white circles (control=7 mm; Gal-3C treated=3 mm) FACS (FIG. 17C) of the GFP-expressing HUVECs from the tumors in the mice revealed significant reduction of HUVECs cells in tumors of Gal-3C-treated compared to control mice.

DESCRIPTION OF THE INVENTION

Figure 1:
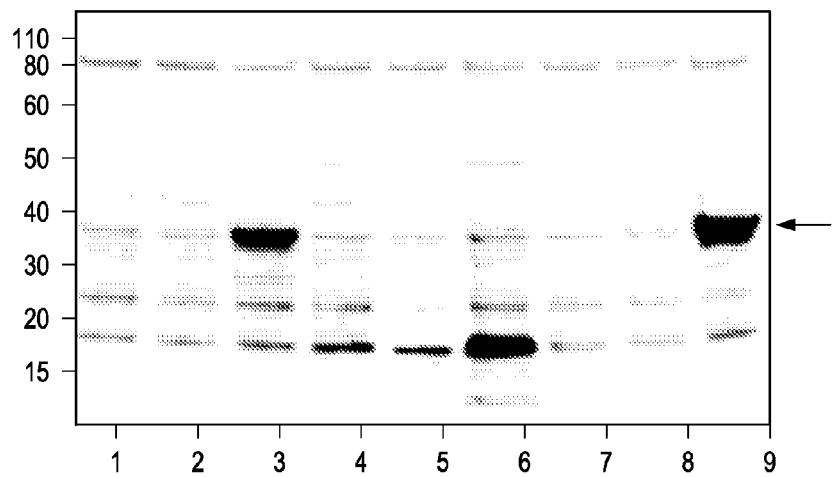
FIG. 1 is an image of a gel showing the Galectin-3 expression levels in MM cell lines. The lysates in each lane are as follows: 1 MM-1S; 2 MM-1RL; 3 NCI-H929; 4 RPMI-8226; 5 Dox-40; 6 LR-5; 7 ARP-1; 8 ARB-B; 9 U266. Galectin-3 monomers are approximately 30 kDa (arrow).

It has now been found, and this forms the subject of the present invention, that the efficacy of galectin-3C may be improved synergistically when it is administered in combination with at least one substance which is therapeutically useful in anticancer treatments and that is a proteasome inhibitor. Synergistic activity of the combination therapy is of particular significance due to the development of drug resistance and the common occurrence of adverse off-target toxicity from treatment with bortezomib.

Our results show that Gal-3C inhibits the growth of MM in a non-obese diabetic/severe combined immunodeficient (NOD/SCID) mouse model of the disease with activity that is comparable to Bor. Combination of Gal-3C with Bor further inhibited tumor growth, which was significantly less than tumors treated with either agent alone. We also provide evidence that the effect of Gal-3C with Boris mediated by the synergistic inhibition of MM-induced angiogenesis and by the inhibition of Bor-mediated NF-KB activation in the MM cells. The translational potential of these results is evident when considering that neovascularization of bone marrow is thought to support the progression of multiple myeloma and that inhibition of angiogenesis is one of the key mechanisms of action of several current frontline drugs for MM therapy, such as thalidomide (63,64), lenalidomide (65) and Bor itself (64,66,67), indicating that inhibition of blood vessel formation might account for the synergistic effect of Gal-3C and Bor observed in vivo.

The above discussion provides a factual basis for the use of the compositions of the present invention. The method used with and the utility of the present invention can be shown by the following non-limiting examples and accompanying figures.

Example 1 discloses Inhibition of U266 Multiple Myeloma Cell Chemotaxis In Vitro. MM is thought to initiate from a single site and then to spread through the circulation to the bone marrow. The homing of the malignant plasma cells to the bone marrow is a hallmark of MM. An agent that could inhibit the spread of MM would be expected to have therapeutic potential.

Cells and Media. The human MM cell lines used were RPMI-8226, U266 (American Type Culture Collection, VA, USA), ARP-1, ARK-B, (gifts from J. Epstein, University of Arkansas for Medical Sciences, Little Rock, Ak., USA). The MM cell lines MM.1S and MM.1RL were generously provided by Dr. Steven T. Rosen, of Northwestern University in Evanston, Ill. 22, and the NCI-H929 cell line was donated by Dr. Steven D. Rosen of the University of California, San Francisco. The 8226/Dox and 8226/LR-5 cell lines were kindly provided by Dr. William S. Dalton of the H. Lee Moffitt Cancer Center and Research Institute in Tampa, Fla. 23. All MM cells were cultured in RPMI-1640 medium supplemented with 10% fetal bovine serum (FBS) in 5% CO2 at 37° C. The 8226/Dox cells were cultured with 40 nM doxorubicin (Sigma-Aldrich, St. Louis, Mo.). The 8226/LR-5 cells were cultured in media containing 5 µM mephalan (Sigma-Aldrich). 8226/Dox and 8226/LR-5 cells were maintained in drug-free medium for 1 week prior to drug sensitivity assays. Human umbilical cord vascular endothelial cells (HUVEC, (American Type Culture Collection, VA, USA) were maintained in EGM-2 medium (Lonza, Huston, Tex.) and were used within 10 passages.

SDS-PAGE and Immunoblot. The MM cell lines were seeded at 300,000 cells/mL and maintained at 37° C. and 5% CO2 for 48 hours. MM cells were harvested and washed twice with phosphate-buffered saline (PBS). Total protein fractions from exponentially growing cells were prepared and analyzed by immunoblot to detect galectin-3. Cell lysis buffer was prepared by mixing 2 ml of M-PER protein extraction buffer (Pierce/Thermo, Rockford, Ill.) with 40 µl of Protease Inhibitor Cocktail (Sigma-Aldrich). The cell suspensions were transferred to a new tube, homogenized using a handheld mortar and pestle, and then rocked at room temperature (RT) for 10 minutes. Extracts were clarified by centrifuging at 12,000×RPM for 15 minutes, diluted to a final concentration of 2.5 mg/ml protein using M-PER, LDS buffer (Invitrogen, Carlsbad, Calif.), and the reducing agent, 2-mercaptoethanol, and then heated at 70° C. for 10 minutes. Proteins were resolved on 4-12% Bis-Tris (Bis(2-hydroxyethyl)-amino-tris (hydroxymethyl)-methane)polyacrylamide gel (Invitrogen) and then electrotransferred onto 0.2 nitrocellulose membrane. After rinsing in PBS-Tween, the blot was stored in protein-free blocking buffer (Pierce/Thermo) at 4° C. overnight. Then, the blot was incubated with anti-galectin-3 antibody 24 (M3/38, Santa Cruz Biotechnology, Santa Cruz, Calif.) diluted 1:200 in blocking buffer at RT for 30 minutes. After washing 5 times with PBS-Tween, the blot was incubated with biotin-conjugated anti-rat IgG diluted 1:2000 in blocking buffer at RT for 1 hour. After 5 washings, the blot was incubated with horseradish peroxidase-conjugated streptavidin diluted 1:1000 in blocking buffer at RT for 20 minutes, and then developed with 3,3',5,5'-tetramethylbenzidine (TMB) with membrane enhancer (KPL; Mandel Scientific, Guelph, Canada). Images were captured with a digital camera and digitally enhanced (Adobe PhotoShop or ImageJ).

Chemotaxis of U266 Cells. U266 cells (400×103/well) were plated in 100-µl cell culture media with and without Gal-3C (0, 0.4, 2.0, 10, and 20 µg/ml) in the top chambers of 24-well transwell inserts with 8-µm pores. Cell culture media (600 µλ) containing the B-cell chemoattractant stromal cell-derived factor (SDF)-1λ (100 ng/ml; R&D Systems, Minneapolis, Minn., USA) was added to the bottom chamber. After 4 hours, the number of U266 cells in the bottom chamber was counted with a FACScan flow cytometer (flux rate on high, a 2 min acquisition gate, and 200 µs resolution).

The proteins derived from a panel of 9 human MM cell lines, namely MM-1S, MM-1RL, NCI-H929, RPMI-8226, 8226/Dox-40, 8226/LR-5, ARP-1, ARK-Band U266, were analyzed by Western blot to detect galectin-3 expression. FIG. 1 indicates that all of the cell lines expressed galectin-3 (~30 kDa). Expression of monomeric galectin-3 appeared to differ greatly, however, with U266 and NCI-H929 having the highest levels.

The M3/38 anti-galectin-3 antibody also stained three other bands that were present in most or all of the samples. Previous studies indicate that this antibody binds to the N-terminal domain of the full-length protein or to an N-terminal fragment of it (68). Bands for two smaller proteins can be observed with one somewhat greater than 20 kDa and the second at about 17 kDa. Galectin-3 is subject to digestion by mammalian metalloproteinases (MMPs) including MMP-2, -9, and -13 that primarily cleave the Ala62-Tyr63 bond yielding a fragment of ~22 kDa containing the CRD and an N-terminal fragment of ~9 kDa(43,69). However, the Gly32-Ala33, P92-S93, and P102-A103 bonds of galectin-3 also are cleaved by MMPs (70).

Another band appears and is of similar intensity in each sample that is approximately 75 kDa in size. Galectin-3 can form non-covalent homodimers and higher order multimers by binding mediated by its N-terminal domain (71). Galectin-3 also can form covalent homodimers through intermolecular disulfide bonds of cysteine (72), and through reactivity with tissue transglutaminase that catalyzes the cross-linking of glutamine with other amino acids (73,74). Prior to electrophoresis, the samples were heated at 70° C. rather than boiled, thus, perhaps the 75 kDa bands may be non-covalent homodimers of galectin-3. Transglutamination should not be affected by reduction, but it is unlikely that disulfide bonds would have survived the treatment of the samples with the reducing agent, 2-mercaptoethanol.

FIG. 1 is an image of a gel showing the Galectin-3 expression levels in MM cell lines. The lysates in each lane are as follows: 1MM-1S; 2 MM-1RL; 3 NCI-H929; 4 RPMI-8226; 5 Dox-40; 6 LR-5; 7 ARP-1; 8 ARB-B; 9 U266. Galectin-3 monomers are approximately 30 kDa (arrow). The immunoblot analysis revealed that all of the cell lines expressed at least a low level of galectin-3, and that NCI-H929 and U266 cells displayed the highest levels (FIG. 1). Varying levels of galectin-3 fragments were observed in the cell lines and were highest in the mephalin-resistant 8226/LR-5 cells. Galectin-3 is a substrate for MMP digestion. Recent data show that breast carcinoma cells transfected to express mutant forms of galectin-3 that were resistant to cleavage by MMPs had a reduced rate of tumor growth, reduced angiogenesis, and decreased apoptosis in xenograft models (36).

Figure 2:
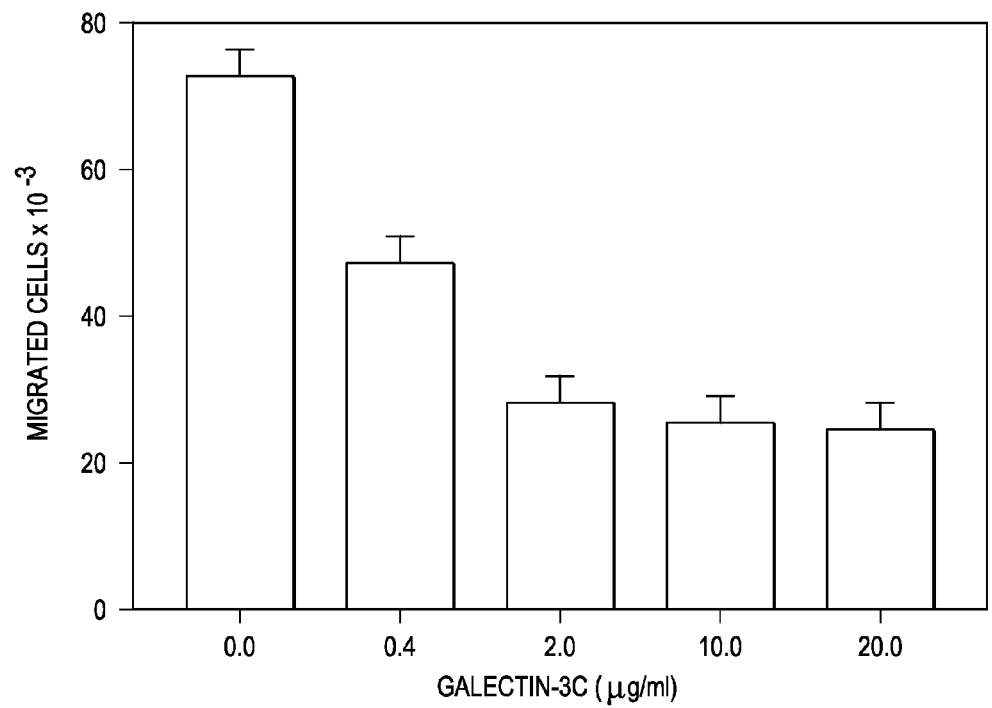
FIG. 2 is a graph of Gal-3C inhibits the chemotaxis of U266 MM cells Gal-3C (0.4, 2, 10, or 20 µg/ml) in bicameral chambers in response to stromal cell-derived factor (SDF)-1α (100 ng/ml). Error bars are ±S.D. and sextuplicate data points are represented (ANOVA with Turkey test P<0.001 for all comparisons to controls).

FIG. 2 is a graph of Gal-3C inhibits the chemotaxis of U266 MM cells Gal-3C (0.4, 2, 10, or 20 µg/ml) in bicameral chambers in response to stromal cell-derived factor (SDF)-1α (100 ng/ml). Error bars are ±S.D. and sextuplicate data points are represented (ANOVA with Turkey test P<0.001 for all comparisons to controls). The presence of Gal-3C in the media with U266 cells in the top chambers of bicameral transwell chambers (FIG. 2) significantly reduced the chemotaxis (migration) of the cells into the bottom chamber containing stromal cell-derived factor (SDF)-1a, a potent lymphocyte chemotactic factor (75). Gal-3C at 2.0 µg/ml inhibited more than 60% of the U266 cell chemotaxis stimulated by the chemokine, SDF-1α. The SDF-1α and its receptor, CXCR4, are regulators of the migration and homing of MM cells to the bone marrow, and possibly may also control egression of MM cells out of the bone marrow (76).

Example 2 discloses the inhibition of angiogenesis in vitro. Angiogenesis is now recognized as a therapeutic target in oncology, and anti-VEGF therapies have shown antitumor efficacy in various types of cancer (77). To continue to grow solid tumors of a few millimeters must induce the proliferation of vascular endothelium and the formation of new blood vessels. Therefore, it is important to discover new agents that inhibit the tumor blood supply (78).

Angiogenesis also plays a key role in the interactions between MM cells and their microenvironment (79, 80) and recent data suggest that VEGF is the main mediator of MM-induced angiogenesis (81, 82). Importantly, increased angiogenesis has been found to be indicative of poor prognosis in MM patients (83-85).

Chemotaxis of HUVEC Cells. Chemotaxis (migration) was analyzed with HUVEC cells as a measure of angiogenic potential as reported (86), using 50×103 cells/well and 24-well transwell inserts with 8-µm pores. The lower chamber was filled with 600-µl EGM-2 medium supplemented with 20% V/V conditioned medium, obtained after treatment of U266 cells with 10 µg/mL Gal-3C, 5 nM Bor, or 10 µg/mL Gal-3C with 5 nM Bor for 48 hour, or with 0.6% VN PBS (Gal-3C and Bor vehicle) as a control. As a negative control, EGM-2 medium alone was used. After incubation for 16 h, cells were removed from the upper chamber, and the migrated cells were visualized on the lower side of the filter after fixing and staining with 30% methanol, 10% acetic and 0.1% Coomassie Brilliant Blue. Next, the filters were extensively washed with water, and then air-dried and photographed using an inverted X71 microscope (Olympus, Center Valley, Pa., USA). The average number of cells in 4 random fields per filter was calculated. The studies were run in triplicate and the results are expressed as a migration index (MI), as follows: MI=number of cells migrated in the presence of conditioned medium/number of cells migrated in the presence of EGM-2 alone. One-way ANOVA and Tukey's post-test indicated that Gal-3C+Bor migration index was significantly different from control (*=p<0.001), while no significant difference was detected between control and Gal-3C or Bor alone (p>0.05). All assays were run in triplicate.

HUVEC Tubule Formation Assay. A tubule formation assay was performed in vitro as described (86) to measure angiogenesis. Briefly, growth factor-reduced Matrigel (Becton Dickinson) was allowed to polymerize in the presence of 30 ng/mL recombinant basic fibroblastic growth factor (bFGF; R&D Systems) for 1 hour at 37° C. (50 µL/well HUVECs (5,000/well), serum-starved for 2 hours prior to trypsinization, were resuspended in 200-µL serum-free EGM-2 supplemented with 20% V/V conditioned medium obtained after treatment of U266 cells with 10 µg/mL Gal-3C, 5 nM Bor, or 10 µg/mL Gal-3C with 5 nM Bor for 48 h, or 0.6% V/V PBS (Gal-3C and Bor vehicle) as a control. The positive control was EGM-2 with 20 ng/mL VEGF (R&D Systems) (87), while the negative control was EGM-2 alone. Cells were seeded onto the polymerized Matrigel and incubated at 37° C. with 5% CO2 for 16 hours to allow tubule formation. The assays were run in triplicate, and pictures were taken with an inverted X71 microscope (Olympus).

ELISA of VEGF and bFGF Levels. The levels of VEGF and bFGF were measured by direct ELISA as follows. Flat-bottom 96-well polycarbonate plates were coated at 4° C. with 50 µL/well cell culture supernatants diluted 1:25 in carbonate coating buffer (0.1 M NaHCO3, 0.1 M NaHCO3, pH 9.5) at 4° C. overnight. Standard curves were obtained with purified recombinant human VEGF and bFGF (both from R&D Systems) serially diluted in coating buffer (10-fold serial dilutions from 1,000 to 0 ng/mL). After removing diluted supernatants or standards, and blocking with PBS supplemented with 1% W/V BSA for 1 hour at room temperature, plates were incubated for 1 hour at room temperature with mouse anti-human VEGF or rabbit anti-human bFGF primary antibodies (2 µg/mL in PBS, 50 µL/well Abeam, Mass., USA). Then, plates were washed twice with PBS with 0.025% V/V Tween-20 (300 µL/well) and incubated at room temperature with anti-mouse or anti-rabbit HRP-labeled secondary antibodies (0.2 µg/mL in PBS, 50 µL/well Abeam, Mass., USA) for 1 hour. The plates were washed thrice with PBS containing 0.025% V/V Tween-20 (300 µL/well), the TMB colorimetric substrate (Thermo Fisher Scientific, Waltham, Mass., USA) was added, and after 5 minutes the absorbance was measured (0.1 s) at 450 nm on a Victor 2 multimodal microplate reader (PerkinElmer, Billerica, Mass., USA). All samples were run in triplicates.

Figure 3A:
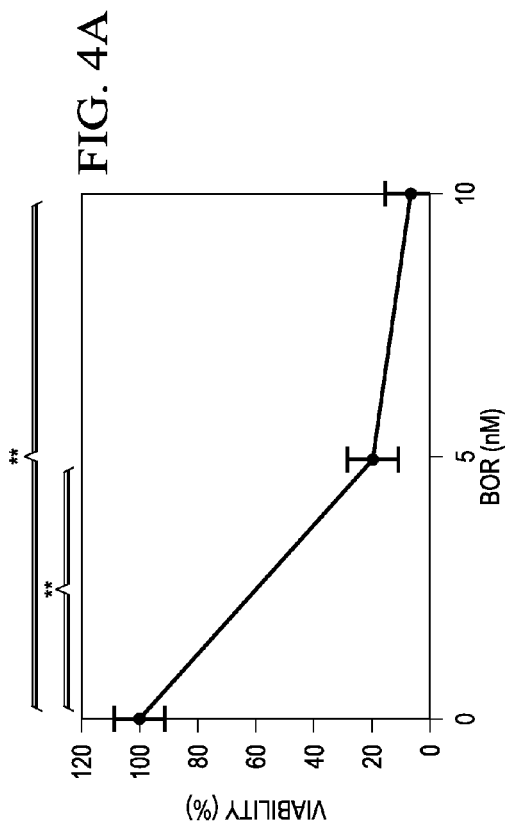
FIG. 3A is a graph of the results from the vascular endothelial cell migration assay.
Figure 3B:
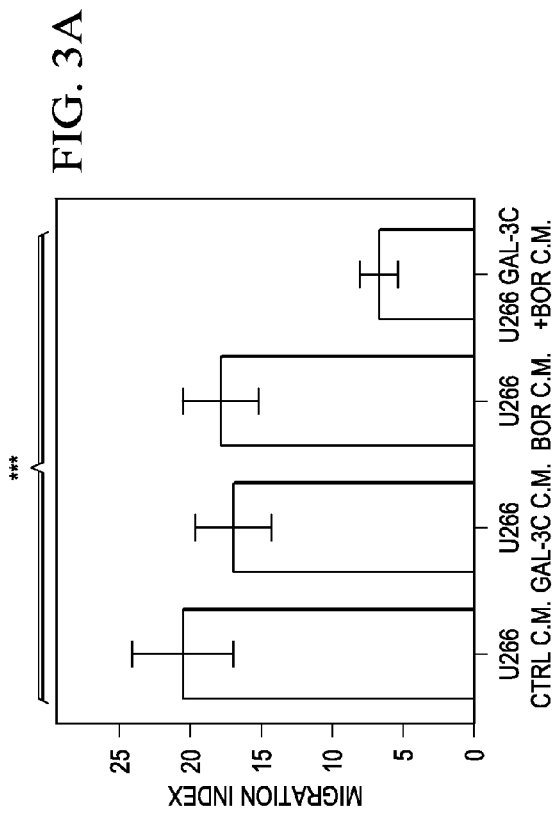
FIG. 3B is an image of the filters. Serum-starved HUVEC were loaded in the upper chambers of Transwell inserts and the bottom chambers contained EBM-2 medium supplemented with 20% VN conditioned media (c.m.) from U266 cultures undergone different treatments: control (ctrl), Galectin-3C (Gal-3C), bortezomib (Bor), or the combination of Gal-3C and bortezomib (Gal-3C with Bor). Mean migration indexes (left; ±95% C.I.) expressed as the number of cells migrated in the presence of the indicated stimulus divided by the number of cells migrated in the presence of EBM-2 alone.

FIG. 3A is a graph of the results from the vascular endothelial cell migration assay. FIG. 3B is an image of the filters. Serum-starved HUVEC were loaded in the upper chambers of Transwell inserts and the bottom chambers contained EBM-2 medium supplemented with 20% VN conditioned media (c.m.) from U266 cultures undergone different treatments: control (ctrl), Galectin-3C (Gal-3C), bortezomib (Bor), or the combination of Gal-3C and bortezomib (Gal-3C with Bor). Mean migration indexes (left; ±95% C.I.) expressed as the number of cells migrated in the presence of the indicated stimulus divided by the number of cells migrated in the presence of EBM-2 alone. Gal-3C and Bor synergistically inhibit endothelial cell migration. To evaluate the effects of Gal-3C on multiple myeloma cell-induced migration of human vascular endothelial cells (HUVEC), a TRANSWELL®-based chemotaxis assay was performed as follows and described above in detail. U266 cells were cultured in the presence of 10 µg/mL Gal-3C, 5 nM Bor or combined treatment. As a control, U266 also were cultured in the presence of PBS (the vehicle of Gal-3C and Bor). After 48 hours, conditioned media derived from different treatments were diluted in EBM-2 medium at the final ratio of 20% and used as chemoattractants for HUVEC cells. Without taking into account cellular uptake the concentration of drugs in the chemotaxis assay were 2 µg/mL Gal-3C and 1 nM Bor. Results of a 16-hour migration assay are displayed in FIG. 3. Single treatments did not produce a significant variation in the migration index, while combined treatment resulted in 70% reduction of the HUVEC migration. The results as shown in FIG. 3 demonstrate a more than additive, synergistic effect from combination treatment with Gal-3C and Borin an in vitro assay of angiogenesis. Statistical analysis of the data using one-way ANOVA and Tukey's post-test indicated that the migration index of Gal-3C with Bor was significantly different from controls (*=p<0.001), while no significant difference was detected between controls and Gal-3C or Bor alone (p>0.05).

Figure 4A:
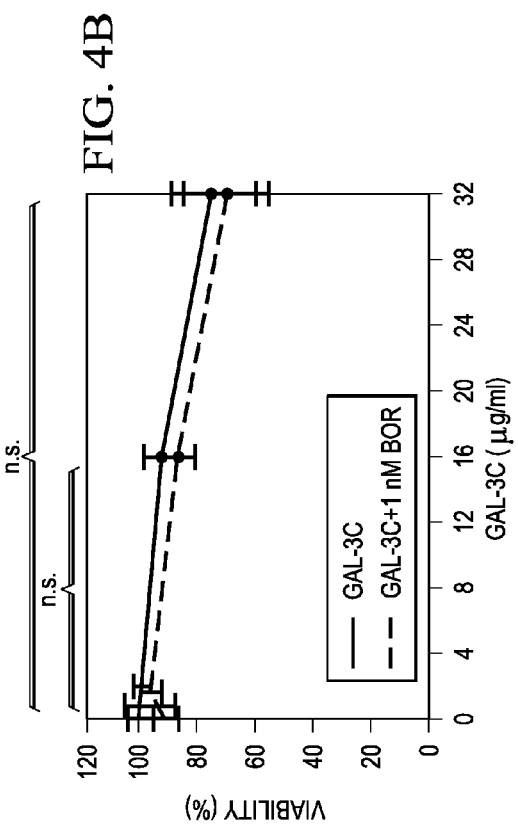
FIGS. 4A and 4B are graphs of the data from the vascular endothelial cell viability assay. Viability was measured as described for U266 cells in studies run in triplicate and displayed as percentage of control (untreated) cells. The graphs show mean values and error bars represent 95% C.I. **=ANOVA Tukey's post test p<O.O1. n.s.=not significant.
Figure 4B:
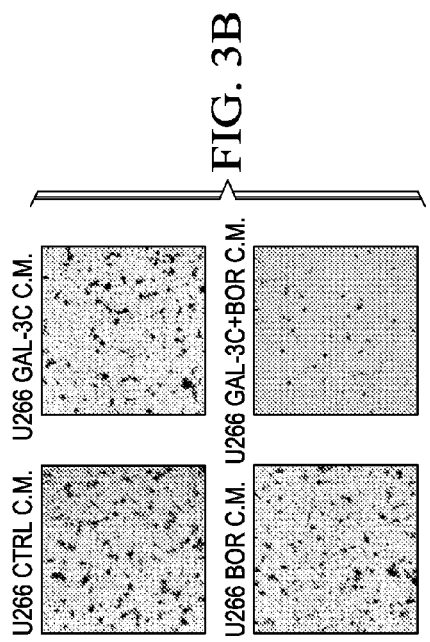

FIGS. 4A and 4B are graphs of the data from the vascular endothelial cell viability assay. Viability was measured as described for U266 cells in studies run in triplicate and displayed as percentage of control (untreated) cells. The graphs show mean values and error bars represent 95% C.I. **=ANOVA Tukey's post test p<O.O1. n.s.=not significant. Gal-3C did not affect endothelial cell viability. To determine if the effects of Gal-3C alone or in combination with Boron vascular endothelial cell migration or secretion were secondary with the primary effect due to reduced cell viability, HUVEC cells were treated with Gal-3C, Bor or treatment with both for 48 h. Viability was measured as described for the U266 cells. Because at the highest concentrations Gal-3C had a mild effect on HUVEC viability and Bor alone showed dramatic inhibition, relatively low concentrations of Gal-3C (2 D g/ml) and Bor (1 nM) were used for the chemotaxis and angiogenesis assays. Results obtained from the HUVEC viability studies that were run in triplicate are depicted in FIG. 4, and are presented as a percentage of control (untreated) cells.

Figure 5:
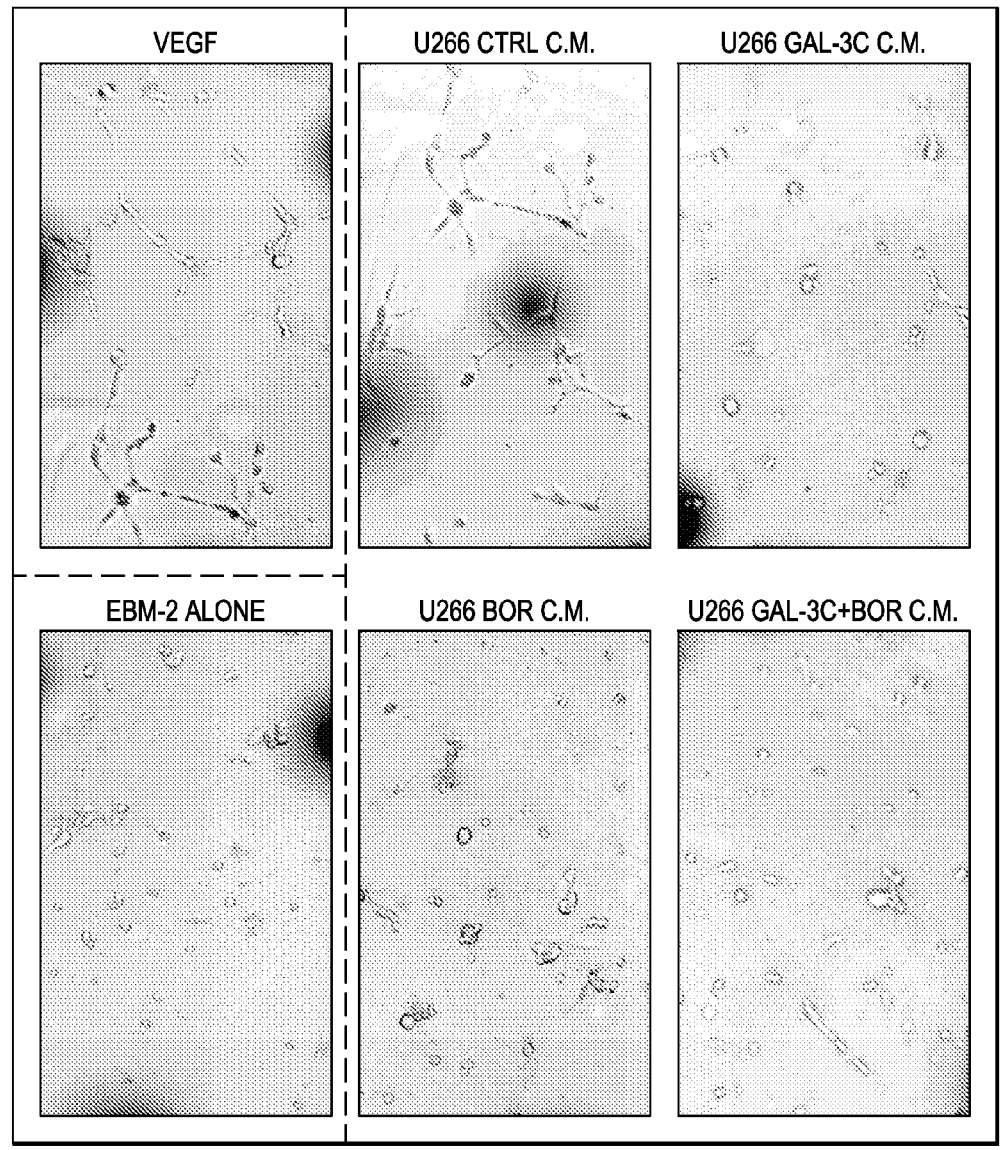
FIG. 5 is an image of the results from the In vitro tubule formation assay having 6 regions. Serum-starved HUVEC were allowed to form tubules on a MATRIGEL™ surface in the presence of VEGF (positive control), EMB-2 medium alone (negative control), or EBM-2 supplemented with 20% V/V U266 conditioned media (c.m.). Representative pictures from 3 comparable studies are shown.

FIG. 5 is an image of the results from the In vitro tubule formation assay having 6 regions. Serum-starved HUVEC were allowed to form tubules on a MATRIGEL™ surface in the presence of VEGF (positive control), EMB-2 medium alone (negative control), or EBM-2 supplemented with 20% V/V U266 conditioned media (c.m.). Representative pictures from 3 comparable studies are shown. Gal-3C and Bor inhibit in vitro angiogenesis. To evaluate the effect of different treatments on the ability of U266 cells to induce angiogenesis, a MATRIGEL™-based tubule formation assay was performed in the presence of U266 conditioned media as described for the chemotaxis assay. Serum-starved ($5 \times 10^3$) HUVEC were seeded on the MATRIGEL™ surface in 200-μL EBM-2 medium supplemented with 20% V/V conditioned medium. Pictures were taken after 16-hour incubation in 5% CO2 at 37° C. The assay was run in triplicate and representative images are depicted in FIG. 5. As a positive control, EBM-2 medium supplemented with 20 ng/mL VEGF was used. Results indicate that treatment with Gal-3C or Bor alone as well as in combination almost completely impaired the potential of U266 cells for induction of angiogenesis, as evidenced by the absence of the organized tubule structures detectable only in untreated (control) U266 conditioned media or VEGF-treated wells. These in vitro results show the potential of Gal-3C and Bor, as well as the combination therapy for inhibition of angiogenesis.

Figure 6A:
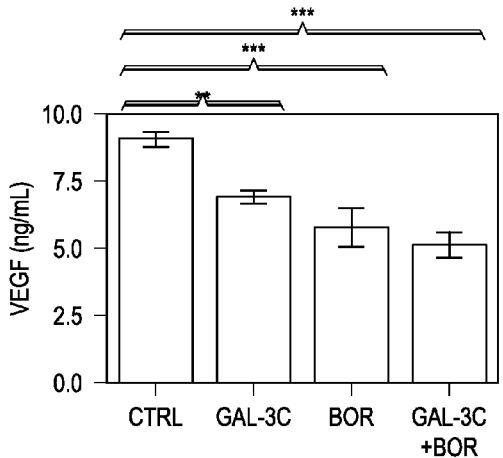
FIGS. 6A and 6B are graphs of ELISA for VEGF and bFGF. After 48 hours in the presence of indicated treatments, the conditioned medium of U266 cells was dilute 1:2 in ELISA coating buffer and used for a direct ELISA assay. Histograms represent mean values of 3 independent studies. Error bars indicate the 95% C.I. Statistical analysis was performed through one-way ANOVA and Tukey's post-test: =p<0.01; *=p<0.001.
Figure 6B:
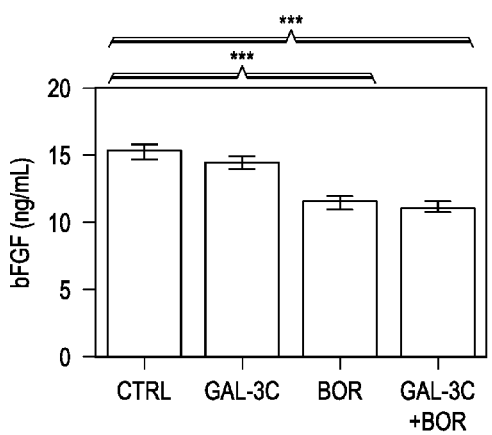

FIGS. 6A and 6B are graphs of ELISA for VEGF and bFGF. After 48 hours in the presence of indicated treatments, the conditioned medium of U266 cells was dilute 1:2 in ELISA coating buffer and used for a direct ELISA assay. Histograms represent mean values of 3 independent studies. Error bars indicate the 95% C.I. Statistical analysis was performed through one-way ANOVA and Tukey's post-test: =p<0.01; *=p<0.001. Gal-3C and Bor affect U266 cell secretion of VEGF and bFGF. As described in detail above, an ELISA was performed to measure the levels of VEGF and bFGF in U266 cell-conditioned medium after 48-hour culture in the presence of 10 μg/mL Gal-3C, 5 nM Bor, or 10 μg/mL Gal-3C with 5 nM Bor, or media (control) with PBS only. The levels of VEGF and bFGF were extrapolated using standard curves obtained by analysis of 10-fold serial dilutions of purified recombinant (Abeam, Mass., USA) proteins (0-1, 000 ng/mL). FIG. 6 shows the results from 3 independent studies: Gal-3C alone significantly reduced VEGF but not bFGF levels, while Bor alone or in combination with Gal3-C significantly reduced both VEGF and bFGF levels. These data on the efficacy of Gal-3C and Borin reducing the secretion of VEGF and bFGF by U266 cells demonstrate in vitro their specificity for inhibition of angiogenesis induced by human multiple myeloma cells.

Our results show that the medium derived from U266 cells treated with Gal-3C in combination with Bor induced significantly less HUVEC migration and angiogenesis as revealed by tubule formation in vitro compared to medium derived from untreated U266 cells (FIGS. 3 and 5). The single treatments significantly inhibited angiogenesis (tubule formation) but not HUVEC migration.

We eliminated the possibility that the inhibition observed was due to reduced HUVEC viability, since Gal-3C did not display significant effects on HUVEC viability at the concentration used in the chemotaxis and angiogenesis assays, and Bor had an effect only at a concentration 5-fold higher (FIG. 4). Furthermore, at the concentration used in HUVEC assays, Bor did not display any effect on HUVEC viability when combined with different concentrations of Gal-3C (FIG. 4).

ELISA assays showed that Gal-3C and Bor alone or combined significantly reduced U266 ability to secrete VEGF, but a significant decrease in bFGF levels was observed only with Bor, alone or combined with Gal-3C (FIG. 6). These observations suggest that the ability of Gal-3C and Bor to hamper HUVEC migration and in vitro angiogenesis is at least in part due to down-regulation of VEGF and bFGF.

EXAMPLE 3 illustrates Gal-3C inhibits proliferation of MM cells. Cell Proliferation (Viability) Assays. Cell proliferation was assessed with a ViaLight Plus Cell Proliferation and Cytotoxicity BioAssay Kit (Lonza, Walkersville, Md., USA) according to the directions of the manufacturer. In brief, myeloma cells were seeded (8,000 per well) in 50 μA of RPMI-1640 with 10% heat-inactivated FBS (growth medium) in 96-well plates. HUVEC cells were seeded (10,000/well) in 50 μl EGM-2 medium in 96-well plates. Gal-3C (2× concentration) in 50 μL of growth medium was added to triplicate wells and the plate kept at the CO2 incubator at 37° C. for 48 hour. For the ViaLight assay, 50 μL of lysis buffer was added to each well, the plate was incubated for 10 minutes, after which 50 μL of cell lysate from each well was transferred to a solid white Lumitrac-200 plate and 50 μL of reconstituted AMR Plus was added. Luminescence was measured with a 1-s integrated setting in a Berthold luminometer after 2 minutes. With Alamar Blue, 10 μL of reagent was added per well and the plate kept in the CO2 incubator for 4 hours. Fluorescence intensity was measured at 590-nm on a Polarstar Galaxy (BMG Labtech, Cary, N.C.) microplate reader. The blank (growth media with 10 μl Alamar Blue) was subtracted from the raw fluorescence to obtain adjusted fluorescence readings. Triplicate data points were analyzed and the data shown are representative of 3 or more studies.

Figure 7A:
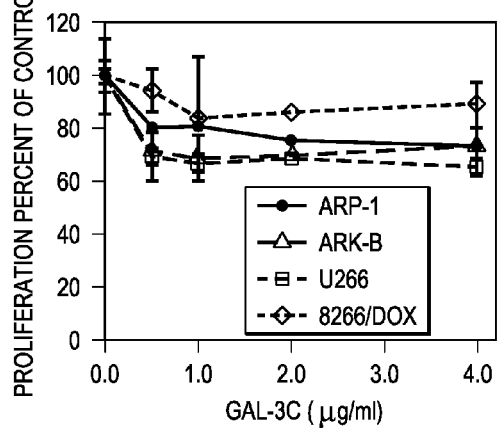
Figure 7A:
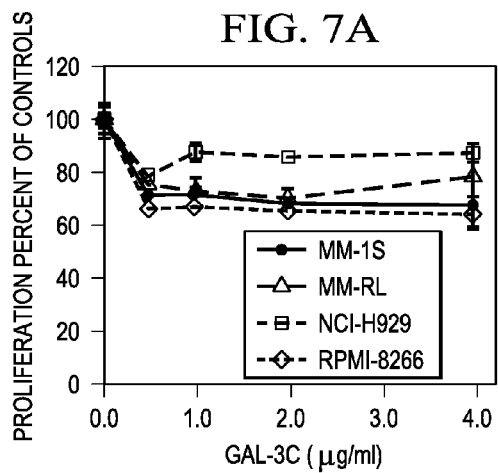

FIGS. 7A and 7B are graphs of the results from proliferation assays with ARP-1, ARK-B, U266, and 8226/Dox, MM-1S, MM-RL, NCI-H929, and RMPI-8266 cells with 0.5, 1, 2, or 4 f-lg/ml Gal-3C compared to control wells over 48 hours. Results from a representative analysis of the effect of Gal-3C on proliferation are shown in FIG. 7. Gal-3C significantly inhibited (defined as P<0.05) the proliferation of all eight cell lines at one or more concentrations, but the overall magnitude of the effects was slight. These data demonstrate that treatment with Gal-3C alone can modestly inhibit the proliferation of MM cells.

Our in vitro analyses indicated that Gal-3C modestly inhibited the proliferation of all 8 MM cell lines tested. However, the sensitivity of the NCI-H929 and U266, which had the highest expression levels of monomeric galectin-3, was no greater than that of the other MM cell lines. In addition, there was little dose-response effect observed from increasing the concentration possibly due to increased Gal-3C multimerization at higher concentrations. Although self-association through the amino-terminal domain when galectin-3 is bound to cell surface glycoconjugates has been widely reported to cause the aggregation of various types of cells (88,89), lactose-inhibitable homodimerization mediated by the CRD has also been reported(90).

EXAMPLE 4 indicates Gal-3C impairs NF-kB activation induced by Bor in U266 cells. Recently, it has been shown that the mechanism of action of Boris more complex than originally thought and can be differ depending on the cell type. Particularly, Bor has been shown to inhibit the canonical NF-kB pathway in some types of cancer, but to induce it by triggering IKK-mediated phosphorylation of IKBα in MM (91). This effect potentially reduces the therapeutic effect of Bor in MM, because NF-kB activation in plasma cells is associated with anti-apoptotic pathways (91). Accordingly, IKK inhibitors potentiate Bor cytotoxicity in vitro and the therapeutic combination of Bor with the IKK inhibitors PS-1145 and MLN120B has been proposed (91). Comparison of NFkB expression by Western blot. U266 and primary human MM cells were treated with Gal-3C, Bor, or both. Equal amounts of lysates of human primary MM and U266 cells and media were fractionated by SDS-PAGE and transferred to nitrocellulose membranes. Primary antibodies were visualized with HRP-coupled goat anti-rabbit or anti-mouse IgGs using an ATK/IKK kit (Cell Signaling Technology, Danvers, Mass.).

To determine whether the AKT/IKK pathway is inhibited by Gal-3C, U266 and human primary MM cells were treated with GAL3C, Bor, or GAL3C plus Bor and analyzed by Western blot using a phospho-specific antibody for the AKT/IKK pathway. Inactive NF-B is located in the cytoplasm where it forms complexes with IKBα. Upon IKK-mediated phosphorylation, IKBα dissociates from the NF-kB complex (p50 and p65 proteins). Free NF-kB is then phosphorylated on serine 529 of the p65 subunit and enters the nucleus where it regulates gene transcription. It is known that in MM cells Bor activates the canonical NF-κB pathway by IKKβ phosphorylation, while Gal3 activates IKKα to induce NF-B pathway. Therefore, the contemporary administration of IKK inhibitors such as GAL3C with Bor is expected to have synergistic effects on MM cytotoxicity.

Figure 10:
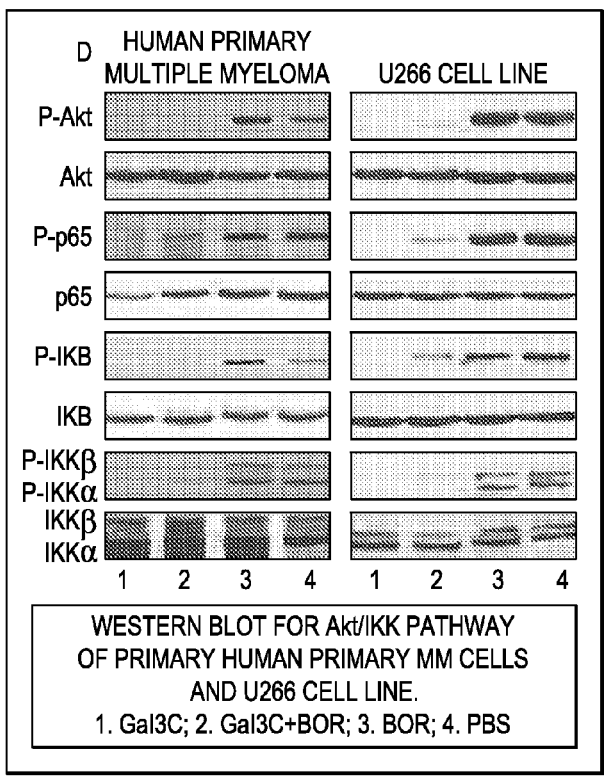
FIG. 10 is an image of a Western blot of proteins in the NF-κB AKT/IKK pathway. The immunoblot shows the analysis of primary MM cells and the U266 cell line after treatment with Gal-3C (lane 1), Gal-3C with Bor (lane 2), Bor (lane 3) or phosphate-buffered saline (PBS; lane 4) as a vehicle control.

The Western blot of U266 and primary human MM cells as shown in FIG. 10 revealed that all of the cells contained high constitutive levels of phosphorylated AKT, IKK, IKB and p65NF-kB. The analysis confirmed the FACS data by revealing the activation (P-p65) of the AKT/IKK pathway in U266 cells and primary human MM cells. It also revealed that the constitutive activation of the AKT-IKK pathway was increased by treatment with Bor. The blot showed that Gal-3C treatment (10 μg/ml) inhibited P-p65, P-Akt, P-IKKβ, and P-IKKα. The blot also showed that in combination treatment Gal-3C inhibited both the constitutive activation of P-p65, P-Akt, P-IKKβ, and P-IKKα and the activation induced by Bor. The results provide a mechanistic rationale for synergistic activity of the two agents in treatment of MM.

Quantification of NF-kappaB Activation by Flow Cytometry. For measurement of NF-kB activation, 200×103 cells were fixed with 2% PFA in ice-cold PBS for 30 minutes. After removal of PFA, cells were permeabilized with 0.3% saponin in PBS on ice for 15 minutes, then washed and resuspended in 50 μL PBS supplemented with 1% BSA. PE-labeled anti-phosphorylated serine 529 p65 antibody (BD Biosciences, San Jose, Calif., USA) or isotype control (final dilution, 1:20) and allowed to incubate on ice in the dark for 30 minutes. Before flow-cytometric analysis cells were washed 3 times in 1-mL cold PBS with 1% BSA.

Figure 8A:
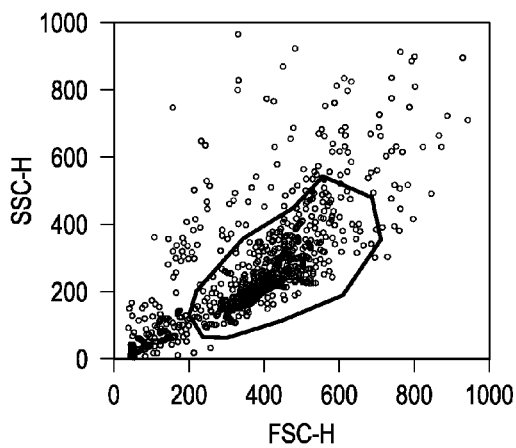
FIG. 8A is a dot-plot of NF-kB activation in U266 cells. After 48 hours in the presence of indicated treatments, the levels of active NF-KB (serine 529 phosphorylated p65 subunit) were evaluated in U266 cells by flow-cytometry.
Figure 8B:
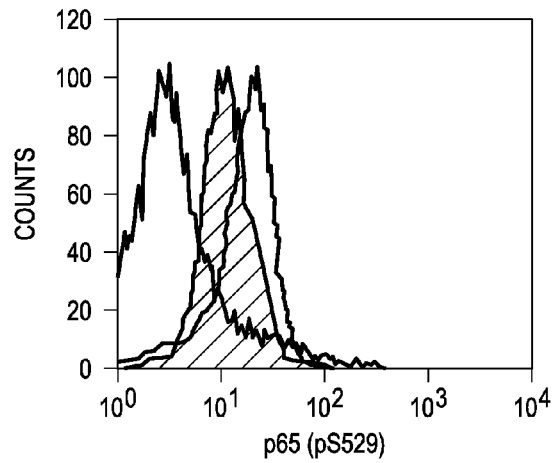
FIG. 8B is a distribution of fluorescence intensity (filled gray histogram: control; bold black line: Gal-3C alone; gray line: Bor alone; thin black line: Gal-3C with Bor).

FIG. 8A is a dot-plot of NF-kB activation in U266 cells. After 48 hours in the presence of indicated treatments, the levels of active NF-KB (serine 529 phosphorylated p65 subunit) were evaluated in U266 cells by flow cytometry. FIG. 8B is a distribution of fluorescence intensity (filled gray histogram: control; bold black line: Gal-3C alone; gray line: Bor alone; thin black line: Gal-3C with Bor). FIG. 8 shows the results of flow cytometric analysis of the phosphorylated active form of NF-KB in U266 cells treated with PBS (control), Gal-3C, Bor, or Gal-3C combined with Bor. While Bor activated NF-kB incrementally, contemporary administration of Gal-3C blocked the Bar-mediated activation. Alone, Gal-3C did not have a significant effect on NF-kB activation. These in vitro data provide evidence on one specific signal transduction pathway whereby Gal-3C facilitates the activity of Bor in treatment of MM.

EXAMPLE 5 shows the efficacy of Galectin-3C Alone and in Combination with Bortezomib in Subcutaneous Mouse Model of Human Multiple Myeloma. Animals: Six-week-old female NOD.CB17-Prkdcscid/J (NOD/SCID) mice were obtained from the Jackson Laboratory (Bar Harbor, Me.). All mice were maintained in filtered-air laminar-flow cabinets under specific pathogen-free conditions. Treatment and care were in accordance with the Institutional Guidelines and the Animal Welfare Assurance Act. All mice were euthanized before they were 10 weeks of age.

Pilot study of in vivo angiogenesis inhibition by Gal-3C. To determine the ability of Gal-3C to inhibit angiogenesis in vivo, 106 HUVECs infected with GFP-expressing rAAV vectors and 107 U266 MM cells were mixed together and suspended in 300 μL Matrigel. The cell mixture was injected subcutaneously into 6 nude mice and allowed to grow for two weeks. Three days after tumor administration, the mice were divided into two groups and one group was implanted with osmotic mini-pumps and treated with Gal-3C as in the study describe above. After 2 weeks, mice were sacrificed, pictures were taken, and the GFP-expressing cells in tumor masses were analyzed by flow cytometry.

Drugs and Mini-pumps: Gal-3C was prepared as previously described. Bortezomib (Bor) was purchased from Millennium Pharmaceuticals (Cambridge, Mass., USA). Doxorubicin and mephalan were obtained from Sigma-Aldrich. The 2000 μL 2002 mini-osmotic pumps designed to deliver 0.5 μL/h were purchased from DURECT Corporation (Cupertino, Calif., USA).

Generating AAV/GFP genome and virus stocks: The adena-associated virus/green fluorescent protein (AAV/GFP) genome was constructed as follows. Briefly, AAV/GFP virus stocks were generated using complementary plasmids in s96-0.8 or pSH3 in HEK293 cells. Lysates of HEK293 cells were used as virus-negative control for mock infections. The DNA was extracted from AAV/GFP virus crude lysates as the sample for titer testing. The titer of virus stocks was determined by real-time PCR. Briefly, we used the plasmid AAV/GFP for the real-time PCR standards. DNA was prepared from 1000-μl, 500-μl and 250-μl volumes of the cell crude lysates of AAV/GFP-infected HEK293 cells and used as template for real-time PCR with 108 encapsulated genomes/ml. Concentration was measured by absorbance at 260 nm. The real-time PCR was performed on an ABI Prism 7000 instrument (Applied Biosystems, Darmstadt, Germany) in a 50-μl reaction volume. Twenty μl of master PCR mix was combined with 10-μl primers. Thermal cycling conditions were as follows: 95° C. for 10 minutes, 45 cycles of 95° C. for 15 seconds, and 55° C. for 1 minute.

Testing Gal-3C and Bonin NOD/SCID mouse model of MM: Prior to injection, U266 cells were washed once in Dulbecco's PBS (Sigma-Aldrich), counted, and adjusted to the appropriate density with additional PBS prior to inoculation. PBS containing a suspension of 1×107 U266 cells was injected subcutaneously into the abdomen of naive NOD/SCID mice. The primary tumors were measured with a pair of calipers once a week. Tumor volume was calculated by the formula width 2×length×0.5, where width was the smallest dimension. The mice were randomly divided into four groups with five mice in each group after 14 days. Control group #1 was subcutaneously implanted in the abdomen with a PBS-only containing 200-μl mini-osmotic pump. Group #2 received a dose of Gal-3C (30 μg/d/mouse) subcutaneously over a 16-day period for a total of 500 μg via a 200-μl mini-osmotic pump implanted abdominally. Group #3 was treated with six doses of 15 μg Borin 50-μl injections via the tail vein on days 1-2, 8-9, and 15-16 for a total of 90 μg. Group #4 received Gal-3C via mini-pump for a total dose of 500 μg Gal-3C (30 μg/d/mouse) plus a total 90 μg Bor in 21 days. Anesthetized animals were euthanized and a post-mortem examination was conducted on the whole animals and dissected organs after 35 days.

Real-time PCR: Total RNA was extracted from the U266 cells, and cells from tissue of the tumors, spleen, kidney, stomach, heart, lung and liver by means of a Trizol-reagent (Sigma-Aldrich) and isolated with the Oligotex mRNA Mini Kit (QIAGEN, Valencia, Calif.), after DNase I digestion. First-strand eDNA synthesis was performed using oligo (dT) 15 primers. PCR primers were as follows: SEQ ID NO: 3: 5'-GCGTACTCTGATACTACAATGATG-3' and SEQ ID NO: 4: 5'-GGG GTTTTGGGTAAAGTCA-3' for AKAP4; and SEQ ID NO: 5: 5-CGGTCGCCACCATGGTGAGC-3' and SEQ ID NO: 6: 5'-GAGCCGTACCTGCTCGACATG-3' for GFP. The sizes of the primers were amplified for AKAP4 to 1100 base pairs (bp) and for GFP to 730 bp, respectively. Positive control was the eDNA of the U266 cells, and negative control was the PCR reaction mixture with water in place of eDNA. RNA integrity in each sample was checked by amplification of a-actin gene segment.

Flow cytometric analysis: The expression of AKAP-4, human IgE, IgG, (heavy chain) k, and A light chains was analyzed by cytofluorimetric techniques as previously described (39). Briefly, cells from liver, blood, U266, and tumor masses were minced under sterile conditions at RT to obtain single-cell suspensions. Minced tumor tissues were placed into 250-ml flasks containing 3-ml of an enzyme solution that consisted of 0.14% collagenase type I (Sigma-Aldrich) and 0.01% DNase (2000 kU/mg of tissue; Sigma-Aldrich) in RPMI 1640, and then incubated on a magnetic-stirring apparatus at 37° C. for 30 minutes. Dissociated tissues were filtered through a 150-μm pore-size nylon mesh to generate a single-cell suspension which was washed twice in RPMI 1640 supplemented with 10% FBS and penicillin/streptomycin. Cell suspensions were distributed into 12×75 mm tubes (5×10$^5$ cells/tube). Cells were incubated with monoclonal antibodies raised against human Ig and AKAP-4 or isotype matching antibodies (BD Biosciences, CA, USA) as negative controls. Analysis was performed using a fluorescence-activated cell scanner (BD Biosciences).

For measurement of NF-kB activation, 200×103 cells were fixed with 2% PFA in ice-cold PBS for 30 min. After removal of PFA, cells were permeabilized with 0.3% saponin in PBS on ice for 15 min, then washed and resuspended in 50 μL PBS supplemented with 1% BSA. PE-labeled anti-phosphorylated serine 529 p65 antibody (BD Biosciences, San Jose, Calif., USA) or isotypic control (final dilution, 1:20) and allowed to incubate on ice in the dark for 30 min. Before flow-cytometric analysis cells were washed 3 times in 1-mL cold PBS with 1% BSA.

ELISA for human AKAP-4, IgG, E, k, and λ light chain: Blood was collected from each mouse once a week, and an enzyme-linked immunoabsorbent assay (ELISA) was performed on the sera to quantify human AKAP-4, IgG, IgE, k, and λ light chain levels as reported 26. Antibodies for immunoglobulins were purchased from BD Biosciences. Anti AKAP-4 antibody was from Santa Cruz Biotechnology. Signal intensity was measured on a Victor 2 multimodal microplate reader (PerkinElmer, Mass., USA) at 450 nm. All samples were run in triplicates.

Figure 9:
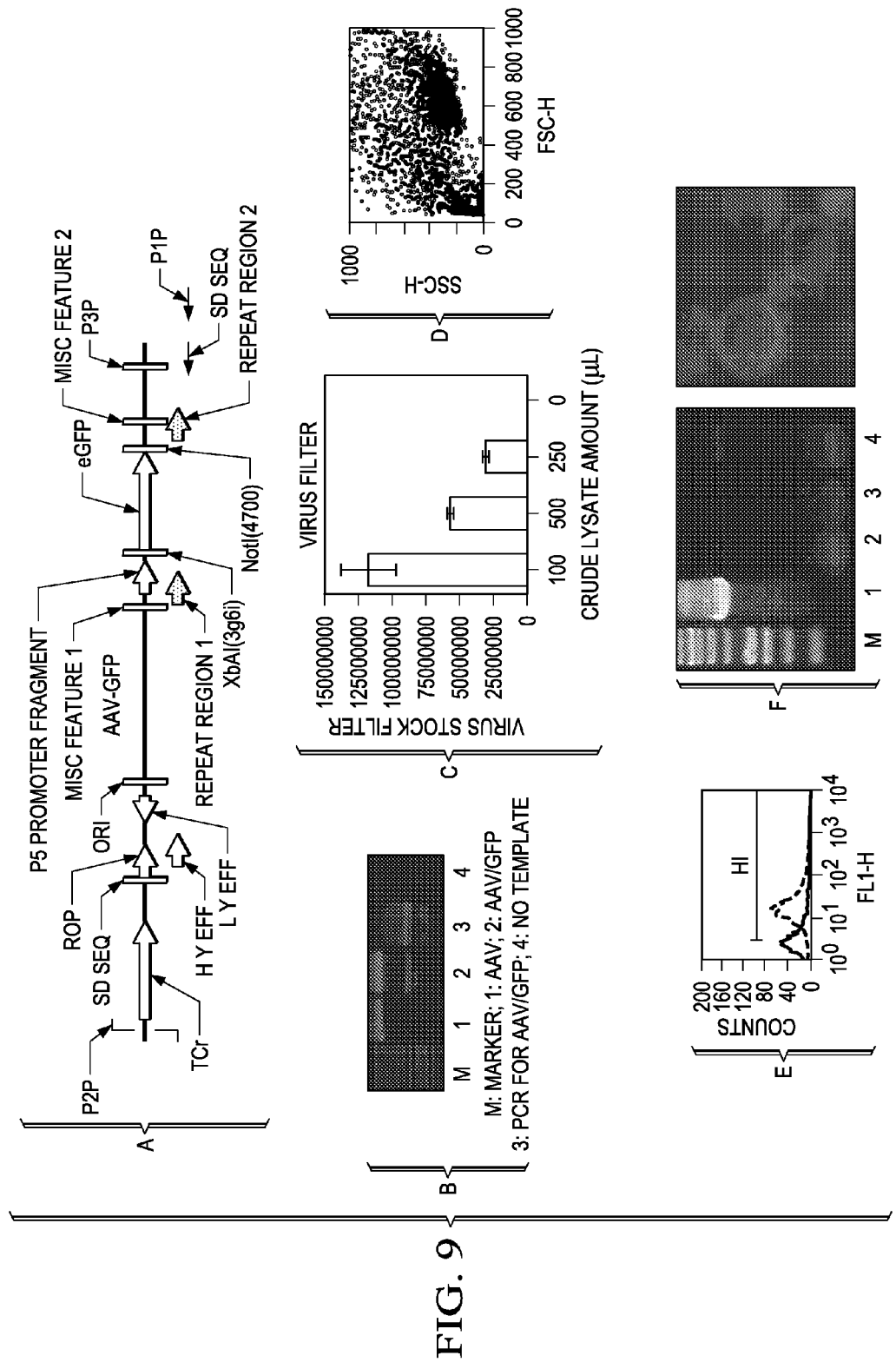
FIGS. 9A-9F are images of the viral vector used and analysis of infection.

FIGS. 9A-9F are images of the viral vector used and analysis of infection. FIG. 9A is a map of the AAV/GFP expression vector showing the restriction sites Xba I and Not I used to insert the GFP coding sequence. FIG. 9B is an image of the ligation of AAV genome and GFP is shown. The GFP insert was cut out from AAV/GFP by Xba I and Not I restriction enzymes (lane 2). FIG. 9C is a graph of the quantification of virus titers by real-time PCR FIG. 9D is a plot of the identification of U266 cells transduced with AAV/GFP by flow cytometry. Grey and black histograms indicate the fluorescence intensity distribution of AAV/GFP- and AAV-transduced U266 cells, respectively. FIG. 9E is a plot of RT-PCR for GFP expression in transduced U266 cells. M: Marker, 1: AAV/GFP plasmid, 2: No RT 3: No template, 4: U266 cells transfected with AAV/GFP. The size of the band from lane 4 was the same as the lane 1. FIG. 9F is an image of the photomicrograph of U266 cells showing fluorescence of AAV/GFP-transduced U266 cells.

Generation and testing of AAV/GFP virus stocks: A structural map of the AAV/GFP vector is presented in FIG. 9A. The restriction sites Xbai and Notl were used to insert the GFP gene downstream of the p5 promoter. FIG. 3B illustrates the identification of AAV/GFP by restriction enzyme analysis. GFP was cut from AAV/GFP by Xbai and Notl enzymes. The titer of virus stocks was determined by real-time PCR (FIG. 9B) to be 108 encapsulated genomes (eg). After generation of the AAV/GFP virus stock, we evaluated the infection of U266 cells. The AAV/GFP vector-infected cells expressed GFP, as confirmed by immunofluorescence labeling, RT-PCR, and cytofluorimetric analysis (FIGS. 9C and 3D).

FIG. 10 is an image of a Western blot of proteins in the NF-κB AKT/IKK pathway. The immunoblot shows the analysis of primary MM cells and the U266 cell line after treatment with Gal-3C (lane 1), Gal-3C with Bor (lane 2), Bor (lane 3) or phosphate-buffered saline (PBS; lane 4) as a vehicle control.

Figure 11:
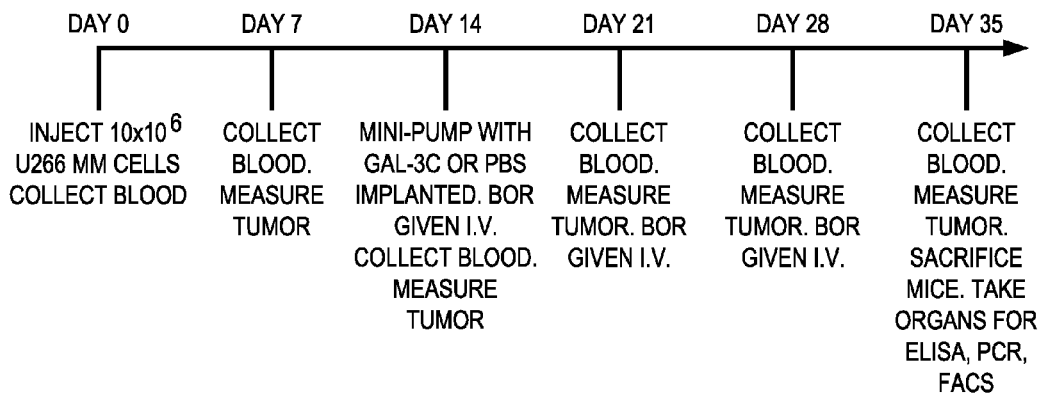
FIG. 11 is a time line of the experimental design and outcome of Gal-3C treatment in NOD/SCID MM xenografts. The diagram shows the timing of tumor challenge, drug administration, and sample collections.
Figure 12:
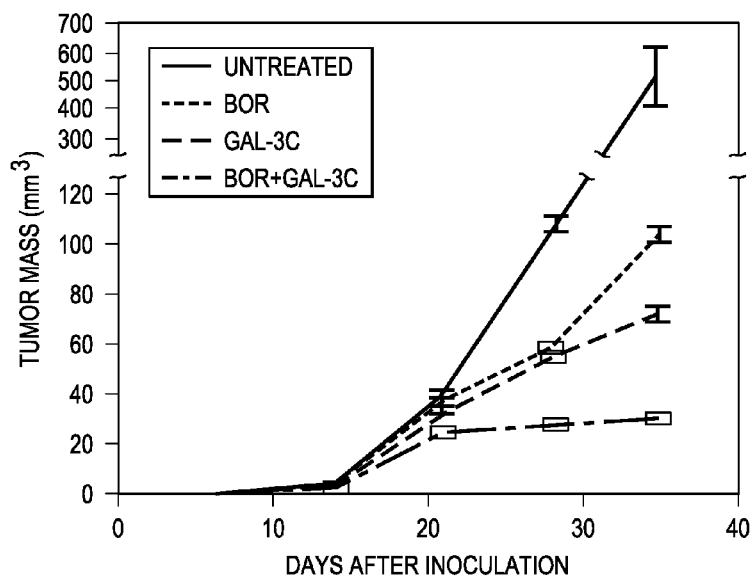
FIG. 12 is a graph of Gal-3C reduces growth of U266 MM subcutaneous tumors as a single agent, and in combination with Bor significantly reduces the MM tumor growth compared to treatment with either agent alone. The graph represents the combination of three separate studies with n=5 per group in each experiment, and the error bars represent ±SEM.

Gal-3C treatment and combination treatment with Bor inhibits the growth of U266 tumors. The sequence of procedures used to establish the U266 MM model in the NOD/SCID mice and to treat the mice with Gal-3C, Bor, and the combination of Gal-3C and Boris shown in FIG. 11. Tumor volumes (FIG. 12) were measured with calipers once weekly. The average tumor volume in Bor treated group was significantly less than in the untreated group from day 28 through day 35 (unpaired t test P<0.001). At day 35, the average tumor volumes of the Gal-3C-only and the Bor-only group were 13.5% and 19.6% that of the untreated controls, respectively. Gal-3C treatment produced a significant reduction of tumor volume compared with Bor starting on day 21 (unpaired t test P<0.001), with a mean difference between the two of 4.431±1.494 mm$^3$, through day 35 when the mean difference was 31.54±4.379 mm3 (unpaired t test P<0.001).

The average tumor volume in the groups receiving the combination of Gal-3C with Bor was significantly less than that of the groups treated with Bor (or with Gal-3C) beginning on day 21 (unpaired t test P<0.001). The maximum effect was observed on day 35, when the combination therapy afforded a reduction of 94% in the mean tumor volume, compared with the untreated group (unpaired t test P<0.001).

FIGS. 13i-13v are images of mice taken before (FIG. 13iv, FIG. 13v) and after (FIGS. 13i-13iii) removal of mini osmotic pumps illustrating the difference between the groups in tumor size after 35 days. Tumors within the white circles and calculated volumes are representative of the groups in the study as follows from left to right, (FIG. 13i) untreated vehicle-only control; (FIG. 13ii) untreated vehicle-only control. (FIG. 13iii) Bor, (FIG. 13iv) Gal-3C treated; and (FIG. 13v) Gal-3C plus Bor.

Figure 13:
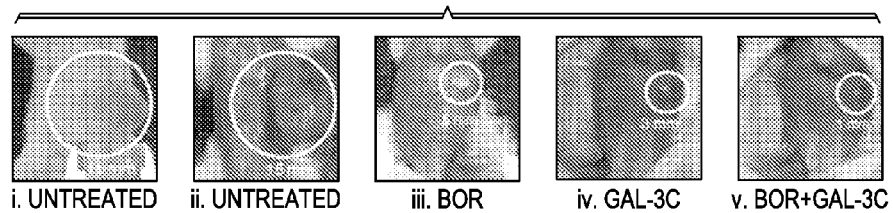
FIGS. 13$i$-13$v$ are images of mice taken before (FIG. 13$iv$, FIG. 13$v$) and after (FIGS. 13$i$-$iii$) removal of mini osmotic pumps illustrating the difference between the groups in tumor size after 35 days. Tumors within the white circles and calculated volumes are representative of the groups in the study as follows from left to right, (FIG. 13$i$) untreated vehicle-only control.

A few of the mice were sacrificed at different time points to directly evaluate the progressive neoplastic growth (FIG. 13). Volumes of the tumors presented by these mice were included in the tumor volume measurement analysis up until the time point when they were sacrificed. These analyses further confirmed that the tumor masses in the Gal-3C plus Bor treatment group were the smallest. The average tumor masses from the group treated with Gal-3C plus Bor was smaller than those of the groups treated with either agent alone (P<0.001).

Figure 14:
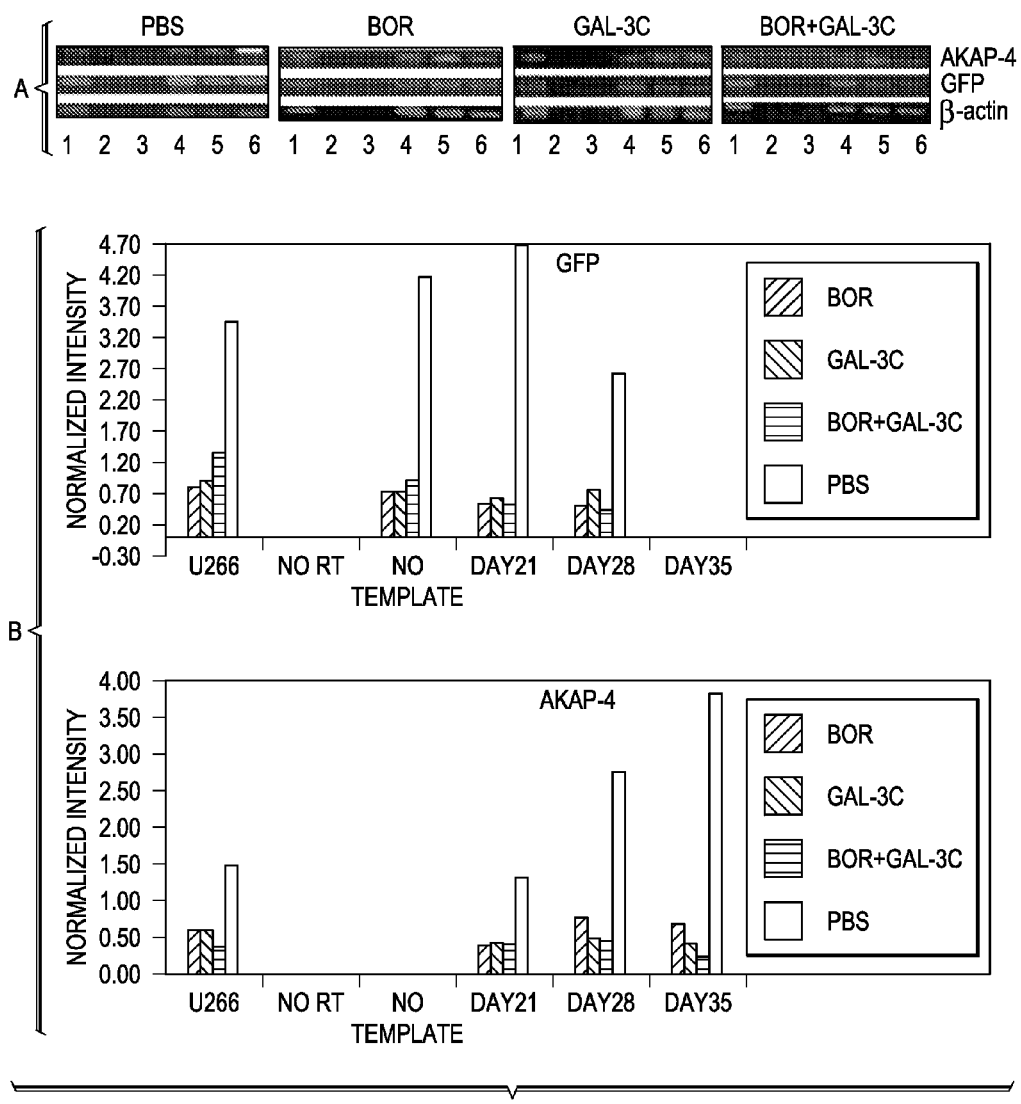
FIG. 14A is an image and FIG. 14B is a graph of the analysis of AKAP-4 and GFP expression by RT-PCR showing the expression of AKAP-4 and GFP in the tumor masses in the four groups (5 mice/group): (1) U266 (2) no RT (3) no template (4) day 21 (5) day 28 (6) day 35. U266 cell line was used as a positive control after 48-hour culture with the indicated treatments.

FIG. 14A is an image and FIG. 14B is a graph of the analysis of AKAP-4 and GFP expression by RT-PCR showing the expression of AKAP-4 and GFP in the tumor masses in the four groups (5 mice/group): (1) U266 (2) no RT (3) no template (4) day 21 (5) day 28 (6) day 35. U266 cell line was used as a positive control after 48-hour culture with the indicated treatments. Specimens of the subcutaneous tumors were analyzed for mRNA encoding AKAP-4 and GFP by RT-PCR weekly. The results (FIG. 14) demonstrated the expression of both GFP and AKAP-4 and confirmed that the tumor masses originated from U266 cells. Kodak 1D software was used to analyze the PCR product band intensity and the relative intensities are presented graphically. Interestingly, the analyses revealed that the expression levels of AKAP-4 and GFP in the Gal-3C plus Bor group were lower than any of the other groups at day 35.

AKAP-4 also was detected in the sera of tumor-bearing mice. Tumor growth was associated with increased AKAP-4 levels in the serum beginning in the PBS group on day 21. The results show the levels of heavy and light chain IgE and AKAP-4 were lower in the treated groups than in the PBS group. At 35 days after inoculation, AKAP-4 in the sera from the combination therapy (Gal-3C plus Bor) group was lower than the PBS group.

FIGS. 15A-15C are graphs of ELISA for human immunoglobulins and AKAP-4 in mice sera The mice were bled at the indicated time point after inoculation of U266 cells, and the levels of igE heavy (FIG. 15A) and light chains (FIG. 15B), and AKAP-4 (FIG. 15C), were determined by ELISA. Each graph is representative of three studies with samples analyzed in triplicates. Tumor expression of human IgE and Igλ is diminished in treated groups. The presence of human immunoglobulin in the sera of the tumor-bearing mice was confirmed by ELISA. The tumors expressed human IgE and Igλ, while human IgG and lgK were undetectable in either the tumors or the sera of the mice. Moreover, the expression levels of igE and Igλ in the treated groups were lower (FIG. 15) than the levels in the controls. The lowest expression levels of igE and Igλ were observed in the tumors of the group treated with Gal-3C with Bor.

Figure 16:
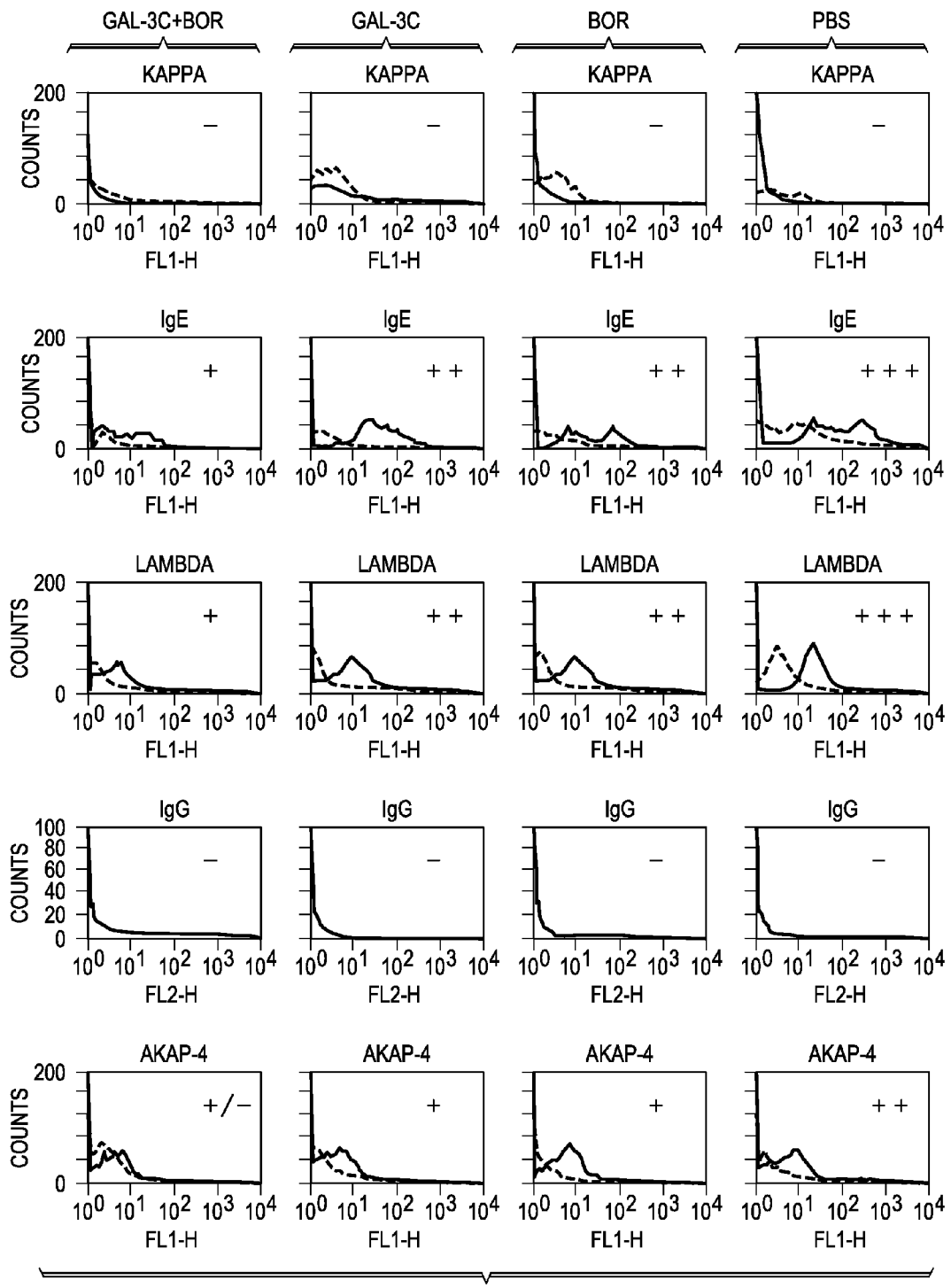
FIG. 16 is an array of plots showing flow cytometric analyses of the expression of igE, IgG, IgK, IgA, and AKAP-4 by cells from tumors of all four groups revealed that IgE, IgA and AKAP-4 were expressed by the tumor cells but not IgK and IgG, and that expression levels of igE, IgA, and AKAP-4 in the PBS control group were the highest, while the levels in cells of the group treated with the combination of Gal-3C with Bor were the lowest. The data represent three independent studies with samples analyzed in triplicates.

FIG. 16 is an array of plots showing flow cytometric analyses of the expression of igE, IgG, IgK, IgA, and AKAP-4 by cells from tumors of all four groups revealed that IgE, IgA and AKAP-4 were expressed by the tumor cells but not IgK and IgG, and that expression levels of igE, IgA, and AKAP-4 in the PBS control group were the highest, while the levels in cells of the group treated with the combination of Gal-3C with Bor were the lowest. The data represent three independent studies with samples analyzed in triplicates. Flow cytometric analyses confirmed the expression of igE and Igλ by the tumors (FIG. 16), and revealed that the highest expression levels of igE, Igλ and AKAP-4 was in the tumors of the PBS-only control group, while the levels of all three were lowest in the group treated with the combination of Gal-3C with Bor, a result also reflecting the relative tumor volumes of the groups.

In vivo based on the measurements of tumor volume, Gal-3C had better efficacy than Bor as a single agent when delivered intravenously using an osmotic mini-pump in a U266 subcutaneous model of MM in NOD/SCID mice (P<0.001). Most importantly for a potential clinical application, the combination of Gal-3C with Bor produced a better response (P<0.001) compared to either agent alone. Within a short time after treatment began, there was only very slight tumor growth in the group treated with the combination therapy. Given the response to Gal-3C and Bor given as single agents, lower doses of Gal-3C and/or Bor would have to be tested to detect a synergistic effect in this model.

In addition to monitoring disease progression by measuring the tumors with calipers, the levels of human IgE and Igλ in the sera of tumor-bearing mice were analyzed and found to be higher in comparison to control mice, consistently with the in vivo expansion of the U266 cells that secrete IgE(92). These results were also confirmed by cytofluorimetric analysis of IgE and Igλ on cells from tumor masses (FIG. 7), and are supported by the findings that IgE and Igλ levels are frequently increased in the serum of MM patients (93). The levels of human IgE and Igλ in both the serum and tumor mass were lower in the Gal-3C plus Bor group compared with all other groups in accordance with the tumor volume measurements.

Contemporaneously, AKAP-4, a member of scaffolding protein family, was used as a tumor marker. Our prior study investigating AKAP-4 expression in MM and in normal tissues demonstrated that it is a novel MM tumor-associated antigen (94). Both AKAP-4 and GFP were detected in all tumor masses, indicating that these proteins could be used to trace tumor progression in the mice. The expression of AKAP-4 and GFP was the lowest in animals treated with Gal-3C plus Bor, mirroring the results obtained with IgE and Igλ and caliper measurements.

Our results show that Gal-3C inhibits the growth of MM in an NOD/SCID mouse model of the disease with activity that is comparable to the proteasome inhibitor, Bor. Combination of Gal-3C with Bor further inhibited tumor growth, which was significantly less than tumors treated with either agent alone. Finally, we provide evidence that the synergistic effect of Gal-3C with Boris mediated by the inhibition of MM-induced angiogenesis and by the inhibition of Bor-mediated NF-KB activation in the MM cells. Gal-3C has previously shown anticancer activity in a mouse model of breast cancer, and is thought to act through inhibition of functionality of galectin-3 which has been strongly implicated in the progression of cancer.

FIGS. 17A-17B are images of representative untreated (FIG. 17A) and Gal-3C treated (FIG. 17B) tumor-bearing nude mice. Arrows indicate s.c. vascularization near tumors shown by white circles (control=7 mm; Gal-3C treated=3 mm) FACS (FIG. 17C) of the GFP-expressing HUVECs from the tumors in the mice revealed significant reduction of HUVECs cells in tumors of Gal-3C-treated compared to control mice.

The ability of Gal-3C to inhibit angiogenesis in vivo was determined in a pilot study. Six mice were injected with 106 HUVECs and 107 U266 MM cells suspended in Matrigel and divided into two groups after two weeks. One group of 3 mice was implanted with osmotic mini-pumps and treated with Gal-3C as described above.

As shown in FIG. 17, image analyses of untreated and Gal-3C treated tumor-bearing nude mice revealed that subcutaneous vascularization near tumors was markedly reduced by Gal-3C treatment. Also as presented FIG. 17, FACS (C) of the cells from tumor masses revealed that there was a significant reduction of GFP-expressing HUVEC cells in tumors of Gal-3C-treated compared to control mice. Mean fluorescence intensity (MFI) of cells from controls was 19.24 compared to 9.4 MFI for Gal-3C treated animals. The results showed that the number of endothelial cells in the tumors was reduced by 48% by Gal-3C treatment. The GFP-expressing HUVECs were 89.3% of the cells in tumor masses of the control animals but were only 46.2% of the tumors in Gal-3C treated animals were GFP-expressing HUVEC. These data clearly show that Gal-3C treatment inhibited angiogenesis of the tumors in vivo.

The invention has been described in an illustrative manner, and it is to be understood that the terminology that has been used is intended to be in the nature of words of description rather than of limitation. Obviously, many modifications and variations of the present invention are possible in light of the above teachings. It is, therefore, to be understood that within the scope of the appended claims, the invention can be practiced otherwise than as specifically described.

REFERENCES (1) Bataille R, Harousseau J L: Multiple myeloma. N Engl J Med 1997; 336:1657-64.
(2) Engelhardt M, Kleber M, Udi J, Wasch R, Spencer A, Patriarca F, Knop S, Bruno B, Gramatzki M, Morabito F, KropffM, Neri A, Sezer 0, Hajek R, Bunjes D, Boccadoro M, Straka C, Cavo M, Polliack A, Einsele H, Palumbo A: Consensus statement from European experts on the diagnosis, management, and treatment of multiple myeloma: from standard therapy to novel approaches. Leuk Lymphoma 2010.
(3) Bergsagel D E: Plasma cell myeloma: biology and treatment. Annu Rev Med 1991; 42:167-78.
(4) Blade J, Carreras E, Rozman C, Sierra J, Rovira M, BatHe M, Valls A, Algara M, Marin P, Urbano-Ispizua A, et al.: [Allogenic bone marrow transplantation in multiple myeloma. Analysis of 12 consecutive cases]. Med Clin (Bare) 1995; 105:1-4.
(5) Sterz J, von Metzler I, Hahne J C, Lamottke B, Rademacher J, Heider U, Terpos E, Sezer 0: The potential of proteasome inhibitors in cancer therapy. Expert Opin Investig Drugs 2008; 17:879-95.
(6) Tsukamoto S, Yokosawa H: Targeting the proteasome pathway. Expert Opin Ther Targets 2009; 13:605-21.
(7) Adams J, Ma Y-T, Stein R, Baevsky M, Grenier L, Plamondon L: Boronic ester and acid compounds. U.S. Pat. No. 5,780,454, 1995.
(8) Adams J, Ma Y-T, Stein R, Baevsky M, Grenier L, Plamondon L: Boronic ester and acid compounds, synthesis and uses U.S. Pat. No. 6,297,217, 2001.
(9) Adams J, Ma Y-T, Stein R, Baevsky M, Grenier L, Plamondon L: Boronic ester and acid compositions U.S. Pat. No. 6,617,317, 2003.
(10) Adams J, Ma Y-T, Stein R, Baevsky M, Grenier L, Plamondon L: Boronic ester and acid compounds, synthesis and uses U.S. Pat. No. 6,747,150, 2004.
(11) Laubach J P, Mitsiades C S, Roccaro A M, Ghobrial I M, Anderson K C, Richardson PG: Clinical challenges associated with bortezomib therapy in multiple myeloma and Waldenstroms Macroglobulinemia. Leuk Lymphoma 2009; 50:694-702.
(12) Einsele H: Bortezomib. Recent Results Cancer Res 2010; 184:173-87.
(13) Richardson P G, Mitsiades C, Ghobrial I, Anderson K: Beyond single-agent bortezomib:combination regimens in relapsed multiple myeloma. Curr Opin Oncol 2006; 18:598-608.
(14) Chauhan D, Li G, Podar K, Hideshima T, Shringarpure R, Catley L, Mitsiades C, Munshi N, Tai YT, Suh N, Gribble G W, Honda T, Schlossman R, Richardson P, Sporn M B, Anderson K C: The bortezomib/proteasome inhibitor PS-341 and triterpenoid CDDO-Im induce synergistic anti-multiple myeloma (MM) activity and overcome bortezomib resistance. Blood 2004; 103:3158-66.
(15) Chauhan D, Li G, Podar K, Hideshima T, Mitsiades C, Schlossman R, Munshi N, Richardson P, Cotter F E, Anderson K C: Targeting mitochondria to overcome conventional and bortezomib/proteasome inhibitor PS-341 resistance in multiple myeloma (MM) cells. Blood 2004; 104: 2458-66.
(16) Ling T, Reddy M, Venkata R, Potts B C, Manam R R, McArthur K A: Total synthesis of salinosporamide A and analogs thereof U.S. Pat. No. 7,842,814, 2010.
(17) Corey E J: Analogs of Salinosporamide A U.S. Pat. No. 7,511,156, 2009.
(18) Myers A G, Sun B, Jackson S R: Analogs of salinosporamide A U.S. Pat. No. 7,511,156.
(19) Chauhan D, Singh A V, Ciccarelli B, Richardson P G, Palladino M A, Anderson K C: Combination of novel proteasome inhibitor NPI-0052 and lenalidomide trigger in vitro and in vivo synergistic cytotoxicity in multiple myeloma. Blood 2010; 115:834-45.
(20) Smyth M, Laidig G: Compounds for enzyme inhibition U.S. Pat. No. 7,417,042, 2008.
(21) Davies A M, Lara P N, Jr., Mack P C, Gandara D R: Incorporating bortezomib into the treatment of lung cancer. Clin Cancer Res 2007; 13:s4647-51.
(22) Davies A M, HoC, Metzger A S, Beckett L A, Christensen S, Tanaka M, Lara P N, Lau D H, Gandara D R: Phase I study of two different schedules of bortezomib and pemetrexed in advanced solid tumors with emphasis on non-small cell lung cancer. J Thorac Oncol 2007; 2:1112-6.
(23) Voortman J, Smit E F, Honeywell R, Kuenen B C, Peters G J, van de Velde H, Giaccone G: A parallel dose-escalation study of weekly and twice-weekly bortezomib in combination with gemcitabine and cisplatin in the first-line treatment of patients with advanced solid tumors. Clin Cancer Res 2007; 13:3642-51.
(24) Voortman J, Checinska A, Giaccone G: The proteasomal and apoptotic phenotype determine bortezomib sensitivity of non-small cell lung cancer cells. Mol Cancer 2007; 6:73.
(25) Dees E C, O'Neil B H, Lindley C M, Collichio F, Carey L A, Collins J, Riordan W J, Ivanova A, Esseltine D, Orlowski R Z: A phase I and pharmacologic study of the combination of bortezomib and pegylated liposomal doxo-

(26) Voutsadakis I A, Patrikidou A, Tsapakidis K, Karagiannaki A, Hatzidaki E, Stathakis N E, Papandreou C N: Additive inhibition of colorectal cancer cell lines by aspirin and bortezomib. Int J Colorectal Dis 2010; 25:795-804.

(27) Shah M A, Power D G, Kindler H L, Holen K D, Kemeny M M, Ilson D H, Tang L, Capanu M, Wright J J, Kelsen D P: A multicenter, phase II study of Bortezomib (PS-341) in patients with unresectable or metastatic gastric and gastroesophageal junction adenocarcinoma. Invest New Drugs 2010.

(28) Stenner F, Liewen H, Zweifel M, Weber A, Tchinda J, Bode B, Samaras P, Bauer S, Knuth A, Renner C: Targeted therapeutic approach for an anaplastic thyroid cancer in vitro and in vivo. Cancer Sci 2008; 99:1847-52.

(29) Mitsiades C S, McMillin D, Kotoula V, Poulaki V, McMullan C, Negri J, Fanourakis G, Tseleni-Balafouta S, Ain K B, Mitsiades N: Antitumor effects of the proteasome inhibitor bortezomib in medullary and anaplastic thyroid carcinoma cells in vitro. J Clin Endocrinol Metab 2006; 91:4013-21.

(30) Raz A, Lotan R: Lectin-like activities associated with human and murine neoplastic cells. Cancer Res 1981; 41:3642-7.

(31) Thijssen V L, Poirier F, Baum L G, Griffioen A W: Galectins in the tumor endothelium: opportunities for combined cancer therapy. Blood 2007; 110:2819-27.

(32) Hasan S S, Ashraf G M, Banu N: Galectins-potential targets for cancer therapy. Cancer Lett 2007; 253:25-330

(33) Liu F T, Rabinovich G A: Galectins as modulators of tumour progression. Nat Rev Cancer 2005; 5:29-41. 15366962 NLM MEDLINE.

(34) Nakahara S, Oka N, Raz A: On the role of galectin-3 in cancer apoptosis. Apoptosis 2005; 10:267-75. 15630413 NLM MEDLINE.

(35) Takenaka Y, Inohara H, Yoshii T, Oshima K, Nakahara S, Akahani S, Honjo Y, Yamamoto Y, Raz A, Kubo T: Malignant transformation of thyroid follicular cells by galectin-3. Cancer Lett 2003; 195:111-9.

(36) Nangia-Makker P, Nakahara S, Hogan V, Raz A: Galectin-3 in apoptosis, a novel therapeutic target. J Bioenerg Biomembr 2007; 39:79-84.

(37) Barondes S H, Cooper D N, Gift M A, Leffler H: Galectins. Structure and function of a large family of animal lectins. J Biol Chem 1994; 269:20807-10.

(38) Barondes S H, Castronovo V, Cooper D N, Cummings R D, Drickamer K, Feizi T, Gitt M A, Hirabayashi J, Hughes C, Kasai K, et al.: Galectins: a family of animal beta-galactoside-binding lectins [letter]. Cell 1994; 76:597-8.

(39) Hsu D K, Suberi R I, Liu F T: Biochemical and biophysical characterization of human recombinant IgE-binding protein, an S-type animal lectin. J. Biol. Chem. 1992; 267: 14167-74.

(40) Massa S M, Cooper D N, Leffler H, Barondes S H: L-29, an endogenous lectin, binds to glycoconjugate ligands with positive cooperativity. Biochemistry 1993; 32:260-7.

(41) Liu F T, Hsu D K, Zuberi R I, Kuwahara I, Chi E Y, Henderson W R, Jr.: Expression and function of galectin-3, a beta-galactoside-binding lectin, in human monocytes and macrophages. Am J Pathol 1995; 147:1016-28.

(42) Liu F T, Hsu D K, Zuberi R I, Hill P N, Shenhav A, Kuwahara I, Chen SS: Modulation of functional properties of galectin-3 by monoclonal antibodies binding to the non-lectin domains. Biochemistry 1996; 35:6073-9.

(43) Ochieng J, Green B, Evans S, James 0, Warfield P: Modulation of the biological functions of galectin-3 by matrix metalloproteinases. Biochim Biophys Acta 1998; 1379:97-106.

(44) Acosta-Rodriguez E V, Montes C L, Motran C C, Zuniga E I, Liu F T, Rabinovich G A, Gruppi A: Galectin-3 mediates IL-4-induced survival and differentiation of B cells: functional cross-talk and implications during Trypanosoma cruzi infection. J Immunol 2004; 172:493-502.

(45) Bernardes E S, Silva N M, Ruas L P, Mineo J R, Loyola A M, Hsu D K, Liu F T, Chammas R, Roque-Barreira M C: Toxoplasma gondii infection reveals a novel regulatory role for galectin-3 in the interface of innate and adaptive immunity. Am J Pathol 2006; 168:1910-20.

(46) Clark A G, Chen S, Zhang H, Brady G F, Ungewitter E K, Bradley J K, Sackey F N, Foster M H: Multifunctional regulators of cell growth are differentially expressed in anergic murine B cells. Mol Immunol 2007; 44:1274-85.

(47) Oliveira F L, Frazao P, Chammas R, Hsu D K, Liu F T, Borojevic R, Takiya C M, El-Cheikh M C: Kinetics of mobilization and differentiation of lymphohematopoietic cells during experimental murine schistosomiasis in galectin-3−/−mice. J Leukoc Biol 2007; 82:300-10.

(48) Hoyer K K, Pang M, Gui D, Shintaku I P, Kuwahara I, Liu F T, Said J W, Baum L G, Teitell M A: An anti-apoptotic role for galectin-3 in diffuse large B-cell lymphomas. Am J Pathol 2004; 164:893-902.

(49) Buttery R, Monaghan H, Salter D M, Sethi T: Galectin-3: differential expression between small-cell and non-small-cellung cancer. Histopathology 2004; 44:339-44.

(50) Miyazaki J, Hokari R, Kato S, Tsuzuki Y, Kawaguchi A, Nagao S, Itoh K, Miura S: Increased expression of galectin-3 in primary gastric cancer and the metastatic lymph nodes. Oncol Rep 2002; 9:1307-12.

(51) Bresalier R S, Byrd J C, Wang L, Raz A: Colon cancer mucin: a new ligand for the beta-galactoside-binding protein galectin-3. Cancer Res 1996; 56:4354-7.

(52) Iurisci I, Tinari N, Natoli C, Angelucci D, Cianchetti E, Iacobelli S: Concentrations of galectin-3 in the sera of normal controls and cancer patients. Clin Cancer Res 2000; 6:1389-93.

(53) Byrd J C, Bresalier R S: Mucins and mucin binding proteins in colorectal cancer. Cancer Metastasis Rev 2004; 23:77-99.

(54) Huang Z L, Liu H Y: [Expression of galectin-3 in liver metastasis of colon cancer and the inhibitory effect of modified citrus pectin]. Nan Fang Yi Ke Da Xue Xue Bao 2008; 28:1358-61.

(55) Kawachi K, Matsushita Y, Yonezawa S, Nakano S, Shirao K, Natsugoe S, Sueyoshi K, Aikou T, Sato E: Galectin-3 expression in various thyroid neoplasms and its possible role in metastasis formation. Hum Pathol 2000; 31:428-33.

(56) Cvejic D, Savin S, Golubovic S, Paunovic I, Tatic S, Havelka M: Galectin-3 and carcinoembryonic antigen expression in medullary thyroid carcinoma: possible relation to tumour progression. Histopathology 2000; 37:530-5.

(57) Fernandez P L, Merino M J, Gomez M, Campo E, Medina T, Castronovo V, Sanjuan X, Cardesa A, Liu F T, Sobel M E: Galectin-3 and laminin expression in neoplastic and non-neoplastic thyroid tissue. J Pathol 1997; 181: 80-6.

(58) Balasubramanian K, Vasudevamurthy R, Venkateshaiah S U, Thomas A, Vishweshwara A, Dharmesh S M: Galectin-3 in urine of cancer patients: stage and tissue specificity. J Cancer Res Clin Oncol 2009; 135:355-63.

(59) Oishi T, Itamochi H, Kigawa J, Kanamori Y, Shimada M, Takahashi M, Shimogai R, Kawaguchi W, Sato S, Terakawa N: Galectin-3 may contribute to Cisplatin resistance in clear cell carcinoma of the ovary. Int J Gynecol Cancer 2007; 17:1040-6.

(60) John C M, Leffler H, Kahl-Knutsson B, Svensson I, Jarvis G A: Truncated galectin-3 inhibits tumor growth and metastasis in orthotopic nude mouse model of human breast cancer. Clin Cancer Res 2003; 9:2374-83.

(61) Oda Y, Kasai K: Purification and characterization of beta-galactoside-binding lectin from chick embryonic skin. Biochim Biophys Acta 1983; 761:237-45.

(62) Jarvis G A, John C M, Leffler H: N-terminally truncated galectin-3 for use in treating cancer. US, 2001.

(63) Rajkumar S V, Gertz M A, Lacy M Q, Dispenzieri A, Fonseca R, Geyer S M, Iturria N, Kumar S, Lust J A, Kyle R A, Greipp P R, Witzig T E: Thalidomide as initial therapy for early-stage myeloma. Leukemia 2003; 17:775-9.

(64) Li W W, Hutnik M, Gehr G: Antiangiogenesis in haematological malignancies. Br J Haematol 2008; 143:622-31.

(65) Kotla V, Goel S, Nischal S, Heuck C, Vivek K, Das B, Verma A: Mechanism of action of lenalidomide in hematological malignancies. J Hematol Oncol 2009; 2:36.

(66) Moschetta M, DiPietro G, Ria R, Gnoni A, Mangialardi G, Guarini A, Ditonno P, Musto P, D'Auria F, Ricciardi M R, Dammacco F, Ribatti D, Vacca A: Bortezomib and zoledronic acid on angiogenic and vasculogenic activities of bone marrow macrophages in patients with multiple myeloma. Eur J Cancer 2010; 46:420-9.

(67) Moschetta M, Cesca M, Pretto F, Giavazzi R: Angiogenesis inhibitors: implications for combination with conventional therapies. Curr Pharm Des 2010; 16:3921-31.

(68) Agrwal N, Sun Q, Wang S Y, Wang J L: Carbohydrate-binding protein 35. I. Properties of the recombinant polypeptide and the individuality of the domains. J Biol Chem 1993; 268:14932-9.

(69) Ochieng J, Fridman R, Nangia-Makker P, Kleiner D E, Liotta L A, Stetler-Stevenson W G, Raz A: Galectin-3 is a novel substrate for human matrix metalloproteinases-2 and -9. Biochemistry 1994; 33:14109-14.

(70) Nangia-Makker P, Raz T, Tait L, Hogan V, Fridman R, Raz A: Galectin-3 cleavage: a novel surrogate marker for matrix metalloproteinase activity in growing breast cancers. Cancer Res 2007; 67:11760-8.

(71) Nieminen J, Kuno A, Hirabayashi J, Sato S: Visualization of galectin-3 oligomerization on the surface of neutrophils and endothelial cells using fluorescence resonance energy transfer. J Biol Chem 2007; 282:1374-83.

(72) Woo H J, Lotz M M, Jung m, Mercurio A M: Carbohydrate-binding protein 35 (Mac-2), a laminin-binding lectin, forms functional dimers using cysteine 186. J Biol Chem 1991; 266:18419-22.

(73) van den Brule F A, Liu F T, Castronovo V: Transglutaminase-mediated oligomerization of galectin-3 modulates human melanoma cell interactions with laminin. Cell Adhes Commun 1998; 5:425-35.

(74) Mehul B, Bawumia S, Hughes R C: Cross-linking of galectin 3, a galactose-binding protein of mammalian cells, by tissue-type transglutaminase. FEBS Lett 1995; 360:160-4.

(75) Bleul C C, Farzan M, Choe H, Parolin C, Clark-Lewis I, Sodroski J, Springer TA: The lymphocyte chemoattractant SDF-1 is a ligand for LESTR/fusin and blocks HN-1 entry. Nature 1996; 382:829-33.

(76) Alsayed Y, Ngo H, Runnels J, Leleu X, Singha U K, Pitsillides C M, Spencer J A, Kimlinger T, Ghobrial J M, Jia X, Lu G, Timm M, Kumar A, Cote D, Veilleux I, Hedin K E, Roodman G D, Witzig T E, Kung A L, Hideshima T, Anderson K C, Lin C P, Ghobrial IM: Mechanisms of regulation of CXCR4/SDF-1 (CXCL12)-dependent migration and homing in multiple myeloma. Blood 2007; 109:2708-17.

(77) Grothey A, Galanis E: Targeting angiogenesis: progress with anti-VEGF treatment with large molecules. Nat Rev Clin Oncol 2009; 6:507-18.

(78) Abdelrahim M, Konduri S, Basha R, Philip P A, Baker C H: Angiogenesis: an update and potential drug approaches (review). Int J Oncol 2010; 36:5-18.

(79) Medinger M, Fischer N, Tzankov A: Vascular endothelial growth factor-related pathways in hemato-lymphoid malignancies. J Oncol 2010; 2010:729725.

(80) Kiziltepe T, Anderson K C, Kutok J L, Jia L, Boucher K M, Saavedra I E, Keefer L K, Shami P J: JS-K has potent anti-angiogenic activity in vitro and inhibits tumour angiogenesis in a multiple myeloma model in vivo. J Pharm Pharmacol 2010; 62:145-51.

(81) Swelam W M, Al Tamimi D M: Biological impact of vascular endothelial growth factor on vessel density and survival in multiple myeloma and plasmacytoma. Pathol Res Pract 2010; 206:753-9.

(82) Giatromanolaki A, Bai M, Margaritis D, Bourantas K L, Koukourakis M I, Sivridis E, Gatter K C: Hypoxia and activated VEGF/receptor pathway in multiple myeloma. Anticancer Res 2010; 30:2831-6.

(83) Rana C, Sharma S, Agrawal V, Singh U: Bone marrow angiogenesis in multiple myeloma and its correlation with clinicopathological factors. Ann Hematol 2010; 89:789-94.

(84) Anargyrou K, Dimopoulos M A, Sezer 0, Terpos E: Novel anti-myeloma agents and angiogenesis. Leuk Lymphoma 2008; 49:677-89.

(85) Rajkumar S V, Witzig T E: A review of angiogenesis and antiangiogenic therapy with thalidomide in multiple myeloma. Cancer Treat Rev 2000; 26:351-62.

(86) Markowska A I, Liu F T, Panjwani N: Galectin-3 is an important mediator of VEGF- and bFGF-mediated angiogenic response. J Exp Med 2010.

(87) Shin W S, Maeng Y S, Jung J W, Min J K, Kwon Y G, Lee S T: Soluble PTK7 inhibits tube formation, migration, and invasion of endothelial cells and angiogenesis. Biochem Biophys Res Commun 2008; 371:793-8.

(88) Zhao Q, Barclay M, Hilkens J, Guo X, Barrow H, Rhodes J M, Yu L G: Interaction between circulating galectin-3 and cancer-associated MUC1 enhances tumour cell homotypic aggregation and prevents anoikis. Mol Cancer 2010; 9:154.

(89) Mina-Osorio P, Soto-Cruz I, Ortega E: A role for galectin-3 in CD13-mediated homotypic aggregation of monocytes. Biochem Biophys Res Commun 2007; 353:605-10.

(90) Kuklinski S, Probstmeier R: Homophilic binding properties of galectin-3: involvement of the carbohydrate recognition domain. J Neurochem 1998; 70:814-23.

(91) Hideshima T, Chauhan D, Kiziltepe T, Ikeda H, Okawa Y, Podar K, Raje N, Protopopov A, Munshi N C, Richardson P G, Carrasco R D, Anderson K C: Biologic sequelae of IKB kinase (IKK) inhibition in multiple myeloma: therapeutic implications. Blood 2009; 113:5228-36.

(92) Sugahara T, Nishimoto S, Morioka Y, Nakano K, Nakano K: White sorghum (Sorghum bicolor (L.) Moench) bran extracts suppressed IgE production by U266 cells. Biosci Biotechnol Biochem 2009; 73:2043-7.

What is claimed is:

1. A pharmaceutical combination having therapeutic synergy comprising:
   an effective amount of galectin-3C and the proteasome inhibitor bortezomib.

2. The pharmaceutical combination of claim 1, wherein the galectin-3C and the proteasome inhibitor are administered separately.

3. The pharmaceutical combination of claim 1, wherein the galectin-3C and the proteasome inhibitor bortezomib are administered immediately or by extended release.

4. A pharmaceutical combination having therapeutic synergy comprising
   an effective amount of galectin-3C and bortezomib to overcome resistance to bortezomib, wherein the galectin-3C and bortezomib are administered separately or simultaneously.

5. The pharmaceutical combination of claim 4, wherein the composition is useful in treating cancer in vivo.

6. The pharmaceutical combination of claim 5, wherein the cancer is multiple myeloma.

7. A pharmaceutical combination having therapeutic synergy comprising an effective amount of galectin-3C and salinosporamide A or carfilzomib.

8. The pharmaceutical combination of claim 7, wherein said combination is useful in treating cancer in vivo, wherein said cancer is multiple myeloma.

9. A pharmaceutical combination comprising an effective amount of galectin-3C and proteasome inhibitor bortezomib to synergistically inhibit angiogenesis.

10. A pharmaceutical combination comprising an effective amount of galectin-3C and a proteasome inhibitor that synergistically inhibit angiogenesis.

11. The pharmaceutical combination of claim 7, wherein the galectin-3C, and the salinosporamide A or the carfilzomib, are administered separately.

12. The pharmaceutical combination of claim 9, wherein the combination of galectin-3C and proteasome inhibitor bortezomib is useful in treating cancer in vivo.

13. The pharmaceutical combination of claim 9, wherein the combination of galectin-3C and proteasome inhibitor bortezomib is useful in treating multiple myeloma in vivo.

* * * * *